United States Patent [19]
Ryan et al.

[11] Patent Number: 5,883,076
[45] Date of Patent: Mar. 16, 1999

[54] SYSTEMIN

[75] Inventors: Clarence A. Ryan, Pullman; Gregory L. Pearce, Palouse; Barry F. McGurl, Seattle, all of Wash.

[73] Assignee: Washington State University Research Foundation, Inc., Pullman, Wash.

[21] Appl. No.: 308,887

[22] Filed: Sep. 19, 1994

Related U.S. Application Data

[63] Continuation-in-part of Ser. No. 855,412, filed as PCT/US93/02428 Mar. 18, 1993, Pat. No. 5,378,819, which is a continuation-in-part of Ser. No. 528,956, which is a continuation-in-part of PCT/US91/03685 May 24, 1991, abandoned.

[51] Int. Cl.⁶ .......................... A61K 38/04; A61K 38/16; A61K 14/415
[52] U.S. Cl. .................... 514/12; 514/13; 530/379
[58] Field of Search ........................ 514/13, 12; 530/379

[56] References Cited

U.S. PATENT DOCUMENTS 4,394,443  7/1983  Weismann et al. .......................... 435/6
5,378,819  1/1995  Ryan et al. .............................. 536/23.1

FOREIGN PATENT DOCUMENTS

A-0 437 320  7/1991  European Pat. Off. ..
WO 91/15585  10/1991  WIPO .

OTHER PUBLICATIONS

Rochaix, J–D, "Plant Molecular Biology—Moving Towards Application," *Trends Biotech.* 10:78–79 (1992).
Chasan, R., "Plant Molecular Biology Blossoms in the Desert," *Plant Cell* 3:1255–1262 (1991).
Culver, J.N. et al., "Tobacco Mosaic Virus Elicitor Coat Protein Genes Produce a Hypersensitive Phenotype in Transgenic *Nicotiana Sylvestris* Plants," *Mol. Plant–Microbe Inter.* 4:458–463 (1991).
Ryan, C.A. et al., "Systemin A. Polypeptide Signal for Proteinase Inhibitor Gene Expression in Plants," *Dev. Plant Pathol.* 2:196–201 (1992).
Baydoun, E.A.–H. et al., "The Immobility of Pectic Substances in Injured Tomato Leaves and its Bearing on the Identity of the Wound Hormone," *Planta* 165:269–276 (1985).
Bidlingmeyer, B.A. et al., "Rapid Analysis of Amino Acids Using Pre–Column Derivatization," *J. Chromatogr.* 336:93–104 (1984).
Bowles, D.J., "Defense–related Proteins in Higher Plants," *Ann. Rev. Biochem.* 59:873–907 (1990).
Bradshaw, H.D. et al., "Systemically wound–responsive genes in poplar trees encode proteins similar to sweet potato sporamins and legume Kunitz trypsin inhibitors," *Plant Mol. Biol.* 14, 51–59 (1989).
Brown, W.E. et al., "Isolation and Characterization of a Wound–Induced Trypsin Inhibitor from Alfalfa Leaves," *Biochemistry* 23:3418–3422 (1984).

Brown, W.E. et al., "Wound–Induced Trypsin Inhibitor from Alfalfa Leaves: Identity as a Member of the Bowman–Birk Inhibitor Family," *Biochemistry* 24:2105–2108 (1984).
Chessin, M. et al., "Alarm Systems in Higher Plants," *The Botanical Review* 56:193–235 (1990).
Davies, E., "Action Potentials as Multifunctional Signals in Plants: A Unifying Hypothesis to Explain Apparently Disparate Wound Responses," *Plant, Cell and Environ.* 10:623–631 (1987).
Douglass, J. et al., "Polyprotein Gene Expression: Generation of Diversity of Neuroendocrine Peptides," *Ann. Rev. Biochem.* 53:665–715 (1984).
Dreyer, D.L. et al., "Chemical Basis of Host–Plant Resistance to Aphids," *Plant, Cell and Environ.* 10:353–361 (1987).
Farmer, E.E. et al., "Interplant Communication: Airborne Methyl Jasmonate Induces Synthesis of Proteinase Inhibitors in Plant Leaves," *Proc. Natl. Acad. Sci. U.S.A.* 87:7713–7716 (1990).
Graham, J.S. et al., "Regulation of Syntheses of Proteinase Inhibitors I and II mRNAs in Leaves of Wounded Tomato Plants," *Planta* 169:399–405 (1986).
Graham, J.S. et al., "Wound–Induced Proteinase Inhibitors from Tomato Leaves," *J. Biol. Chem.* 260:6555–6560 (1985).
Green, T.R. et al., "Wound–Induced Proteinase Inhibitor in Plant Leaves: A Possible Defense Mechanism against Insects," *Science* 175:776–777 (1972).
Hammond–Kosack, K.E. et al., "Systemic Accumulation of Novel Proteins in the Apoplast of the Leaves of Potato Plants following Root Invasion by the Cyst–Nematode *Globodera rostochiensis*," *Physiol. Mol. Plant Path.* 35:495–506 (1989).
Harris, R.B., "Processing of Pro–hormone Precursor Proteins," *Arch. Biochem. Biophys.* 275:315–333 (1989).

(List continued on next page.)

*Primary Examiner*—Charles L. Patterson, Jr.
*Attorney, Agent, or Firm*—Harness, Dickey & Pierce, P.L.C.

[57] ABSTRACT

Systemin, an 18 amino acid peptide hormone and first polypeptide hormone found in plants, induces expression of defense genes in plants wounded mechanically or by predators including herbivores, insects, bacteria and viruses. The precursor for systemin is encoded as a 200 amino acid prosystemin molecule that has the systemin peptide sequence located near the carboxyl-terminus. Both a 951 bp cDNA for prosystemin and 4526 bp genomic DNA were cloned and the organization of the gene was determined. Transgenic plants constructed with antisense prosystemin DNA fail to mount a defensive response to wounding. Transgenic plants constructed with increased copy number of prosystemin genes exhibit increased resistance to wounding. Insect larval that feed on transgenic plants constructed with increased copy number of prosystemin genes exhibit decreased growth weight compared to larval that feed on wild type plants. A tomato systemin polypeptide has an amino acid sequence $NH_3$-AVQSKPPSKRDPPKMQTD-$COO^-$.

6 Claims, 28 Drawing Sheets

OTHER PUBLICATIONS

Hilder, V.A. et al., "A Novel Mechanism of Insect Resistance Engineered into Tobacco," *Nature* 330:160–163 (1987).

Hopp, T.P. et al., "Prediction of Protein Antigenic Determinants from Animo Acid Sequences," PNAS (USA) 78:3824–3826 (1981).

Johnson, R. et al., "Expression of Proteinase Inhibitors I and II mRNAs in Transgenic Tobacco Plants: Effects on Natural Defense Against *Manduca sexta* Larvae," PNAS (USA) 86:9871–9875 (1989).

Jung, L.J. et al., "Peptide Processing and Targeting in the Neuronal Secretory Pathway," *Science* 251:1330–1335 (1991).

King, R.W. et al., "Enhancement of Phtoem Exudation from Cut Petioles by Chelating Agents," *Plant Physiol.* 53:96–103 (1974).

Kopp, M.J. et al, "Host–Pathogen Interactions," *Plant Physiol.* 90:208–216 (1990).

Kuc, J. et al., "Fungal Regulation of Disease Resistance Mechanisms in Plants," 76:767–784 (1984).

Lutcke, H.A. et al., "Selection of AUG Initiation Codons Differs in Plants and Animals," EMBO J. 6:43–48 (1987).

McGurl, B. et al., "The Organization of the Prosystemin Gene," *Plant Mol. Biol.,* submitted (no date).

Pearce, G. et al., "A Polypeptide from Tomato Leaves Induces Wound–Inducible Proteinase Inhibitor Proteins," *Science* 253–895–898 (1991).

Pena–Cortes, H. et al., "Abscisic Acid is Involved in the Wound–Induced Expression of the *Proteinase Inhibitor II Gene in Potato and Tomato*," PNAS (USA) 86:9851–9855 (1989).

Roby, D. et al., "Cell Surfaces in Plant Micro–Organism Interactions. VIII. Increased Proteinase Inhibitor Activity in Melon Plants in Response to Infection by *Colletotrichum lagenarium* or to Treatment with an Elicitor Fraction from this Fungus," *Physiol. Mol. Pl. Pathol.* 30:453–460 (1987).

Rogers, S.O. et al., "Extraction of DNA from Milligram Amounts of Fresh, Herbarium and Mummified Plant Tissues," *Plant Mol. Biol.* 5:69–76 (1985).

Ryan, C.A. "Protease Inhibitors in Plants: Genes for Improviing Defenses Against Insects and Pathogens," *Ann. Rev. Phytopathol.* 28:425–449 (1990).

Ryan, C.A., "Proteinase Inhibitors in Plant Leaves: A Biochemical Model for Pest–Induced Natural Plant Protection," TIBS 3:148–150 (1978).

Ryan, C.A. "An Inducible Protein in Potato and Tomato Leaflets," *Plant Physiol.* 43: 1880–1881 (1968).

Ryan, C.A. et al., "Oligosaccharide Signals in Plants: A Current Assessment," *Annu. Rev. Plant. Physiol. Mol. Bio.* 42:651–674 (1991).

Ryan, C.A., "Quantitative Determination of Soluble Cellular Proteins by Radial Diffusion in Agar Gels Containing Antibodies," *Anal. Biochem.* 19:434–440 (1967).

Schechter, I. et al., "On the Size of the Active Site in Proteases. I. Papain," *Biochem. Biophys. Res. Commun.* 27:157–162 (1967).

Smith, P.K. et al., "Measurement of Protein Using Bicinchoninic Acid," *Anal. Biochem.* 150:76–85 (1985).

Strydorn, D.J. et al., "Amino Acid Sequence of Bovine Brain Derived Class 1 Heparin–Binding Growth Factor," *Biochemistry* 25:945–951 (1985).

Thain, J.F. et al., "Oligosaccharides that Induce Proteinase Inhibitor Activity in Tomato Plants Cause Depolarization of Tomato Leaf Cells," *Plant Cell and Environ.* 13:569–574 (1990).

Trautman, R. et al., "Data Processing for Radial Immunodiffusion," *Immunochemistry* 8:901–916 (1971).

```
          1    5        10       15  18
⁺H₃N-AVQSKPPSKRDPPKMQTD-COO⁻
```

FIGURE 3

FIG. 5A.
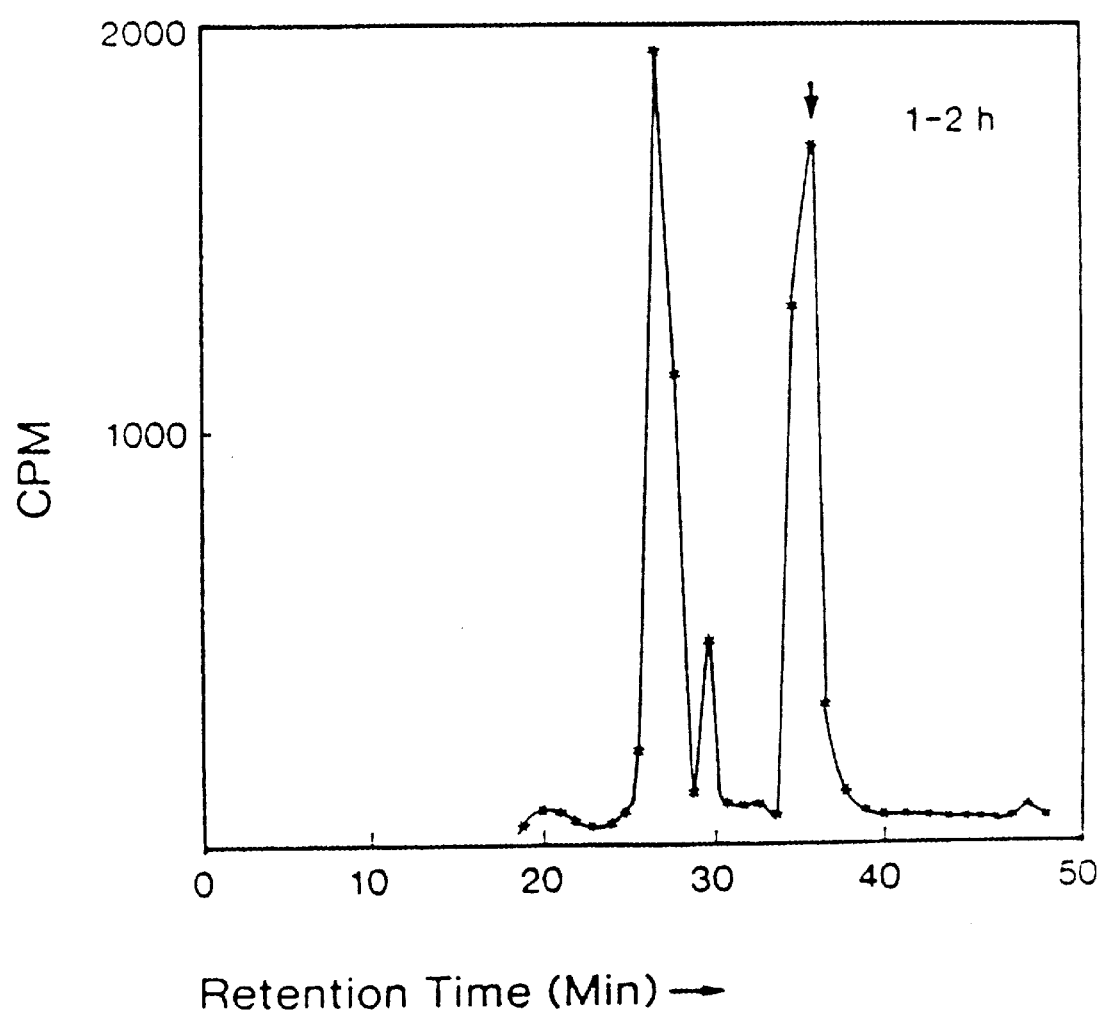
FIG. 5B.

```
Met Gly Thr Pro Ser Tyr Asp Ile Lys Asn Lys Gly Asp Asp Met Gln
1               5                   10                  15
Glu Glu Pro Lys Val Lys Leu His His Glu Lys Gly Gly Asp Glu Lys
            20                  25                  30
Glu Lys Ile Ile Glu Lys Glu Thr Pro Ser Gln Asp Ile Asn Asn Lys
            35                  40                  45
Asp Thr Ile Ser Ser Tyr Val Leu Arg Asp Asp Thr Gln Glu Ile Pro
        50                  55                  60
Lys Met Glu His Glu Glu Gly Gly Tyr Val Lys Glu Lys Ile Val Glu
65                  70                  75                  80
Lys Glu Thr Ile Ser Gln Tyr Ile Ile Lys Ile Glu Gly Asp Asp Asp
                85                  90                  95
Ala Gln Glu Lys Leu Lys Val Glu Tyr Glu Glu Glu Glu Tyr Glu Lys
            100                 105                 110
Glu Lys Ile Val Glu Lys Glu Thr Pro Ser Gln Asp Ile Asn Asn Lys
        115                 120                 125
Gly Asp Asp Ala Gln Glu Lys Pro Lys Val Glu His Glu Glu Gly Asp
    130                 135                 140
Asp Lys Glu Thr Pro Ser Gln Asp Ile Ile Lys Met Glu Gly Glu Gly
145                 150                 155                 160
Ala Leu Glu Ile Thr Lys Val Val Cys Glu Lys Ile Ile Val Arg Glu
                165                 170                 175
Asp Leu Ala Val Gln Ser Lys Pro Pro Ser Lys Arg Asp Pro Pro Lys
            180                 185                 190
Met Gln Thr Asp Asn Asn Lys Leu
    195                 200
```

FIGURE 6

```
  60  .AAAATTAAATTGATATTTGGTTTAACTCGATTTTCCATGAACACCCTTAGTGATGAGT        59
                 10              30                 50

60  ATATAAAGCTCAGCTCATGAAGAGTTGAAATAAACTAAGAAAACCATGGAACTCCTTCA       119
                 70              90                110       MetGlyThrProSer   5

120  TATGATATCAAAAACAAAGGAGATGACATGCAAGAAGAACCAAAGGTGAAACTTCACCAT      179
      TyrAspIleLysLysAsnLysGlyAspMetGlnGluGluProLysValLysLeuHisHis       25
                130             150                170

180  GAGAAGGGAGGAGAGATGAAAAGGAAAAATAATTGAAAAAGAGACTCCATCCCAAGATATC     239
      GluLysGlyGlyAspGluLysGluLysLysGluLysIleIleGluLysGluThrProSerGlnAspIle  45
                190             210                230

240  AACAACAAAGATACCATCTCTTCATATGTTTTAAGAGATGATACACAAGAAATACCAAAG      299
      AsnAsnLysAspThrIleSerSerTyrValLeuArgAspAspThrGlnGluIleProLys      65
                250             270                290

300  ATGAACATGAGGAGGAGGATATGTAAAGGAGAAAATTGTTGAAAAGGAGACTATATCC       359
      MetGluHisGluGluGluGlyTyrValLysGluLysIleValLysGluLysGluThrIleSer    85
                310             330                350

360  CAATATATCATCAAGATTGAAGGAGATGATGCACAAGAAAAACTAAAGGTTGAGTAT        419
      GlnTyrIleIleLysIleGluGlyAspAspAlaGlnGluLysLeuLysValGluTyr        105
                370             390                410
```

FIGURE 7A

```
       420                430                                  450                              470
       106  GAGGAGAAGAATATGAAAAAGAGAAAATAGTTGAAAAAGAGACTCCATCCAAGATATC  479
            GluGluGluGluTyrGluLysGluLysIleValGluLysGluThrProSerGlnAspIle  125

480                490                510                530
       126  AACAACAAGGAGATGATGCACAAGAAAAACCAAGGTGGAACATGGAAGGAGATGAC    539
            AsnAsnLysGlyAspAspAlaGlnGluLysProLysValGluHisGluGluGlyAspAsp  145

540                550                570                590
       146  AAAGAGACTCCATCCAAGATATCATCAAGATGGAAGGGAGGGTGCACTAGAAATAACA  599
            LysGluThrProSerGlnAspIleIleLysMetGluGlyGluGlyAlaLeuGluIleThr  165

600                610                630                650
       166  AAGGTGGTATGTGAGAAAATTATAGTACGAGAAGATCTTGCTGTTCAATCAAAACCTCCA  659
            LysValValCysGluLysIleIleValArgGluAspLeuAlaValGlnSerLysProPro  185

660                670                690                710
       186  TCAAAGGCGTGATCCTCCCAAAATGCAAACAGACAATAATAAACTCTAGAAACATCCAAA  719
            SerLysArgAspProProLysMetGlnThrAspAsnAsnLysLeu 720                730                750                770
            AAAATTAATAATAAAAAATTATAATTCAGAACGATAAAGTAAAAATTCTGAATTGTCT    779

780                790                810                830
            CCCGTTAGAAAAGTAACTTCAAATAAATATTTGTCTTTCTTTGTATTTCAAGTGTAAT    839

840                850                870                890
            TTGGTTATTGTACTTTGAGAAGCTTTCTTTAGATTGTTATGTACTTGTATTGCTTCTTT  899

900                910                930                950
            CTTTTGGCTTATTTATATAATAAATAAAAAATAAATAAATATCTAAAGAT    951
```

FIGURE 7B

```
  1  AAAATTAAATTTGATATTTGGTTTAACTCGATTTTCCATGAACACCCTTAGTGATGAGTATATAAAGCTCAGCTCATGAAGAGTTGAAATAAACTAAGAA
         Exon 1
101  AACCATGGAACTCCTTCATATGATATCAAAAACAAAGGTATCATTTCTTTATATGCCTAAGTATATATTTATTTATATATTTTGTAACTAAAATTTTAT
                                                                                                Exon 2
201  ATTAAAATCAACAAGTGAGAGTTTAACAAAAATCATATTAAAGAAAAAAAATATATTAATTTTTAATCATGGTATTATCCTCCAGGAGAGATGACATGCAAG
301  AAGAACCAAGGTGAAACTTCACCATGAGAGTAACTTAGTTTCTCCTTTTTCTTTTTTCAACTTCTCTTTATATATTTTCTAAATTTTTTTATAT
401  TATAATGTTCAAATGGTCTCTCATTTCTCTAATTAATAATGTGTCTGAATCGGCCATGTTATTTATGTTAGATTTAATACATTGTTAGTAAATGT
501  TAGAATACTGACTCCCAAATTCGGCTTAAGGAACAAGTATATTTCATGTGTTTCTTTGCAGATAACAATAATTATGTTTGTAAAGCAAATAAAATAATAA
601  CATAATATTTATCGTAGAAAACTCCAACTCATTATTTAGATATTTGCTTTAATTATACTTTTTTAAACATGATAAATTATTTCTGTT
701  AGACATTTTCGATTCATTTTTTTTTACAAAAATTGTATTTGCTCTCAAACGTTTACTAGTTAGTTAAGTTAACTATACAAAATATGTCATCTCATTTG
801  ATTATATACATCAGGCTCAATTAAAACATATTGGAGATATGGAGATTTTACGATTCATTAACACTAATGTGTATAGTTAGAAAATGTCAAATATTCAAA
901  TGGTTAACTTTTCTGTATAATTGACATTTGAAACTATATGTTTAATTATAACAAACCGTAATCAAATGTTCAAATAAAATTGAATGACAATAGGTATAAG

FIGURE 8A1
```

```
1001  GAGCTATCAATATATTAGCTCTCTTGATTCAACTTATTTACCGTTATATAATTAAATAATGACTCGTTAATTGATTAATTTTTTTACTCACGTGAAATGA
1101  TTTAATCAACTCATTTATCACCCTTATTTACGACTCATGTAGAATAATGTTCTTTATACTTGTATACAATTTACTCGGATATTTTTTTAAATTTTTTT
1201  TATGTTTAATTAAATACTATTAAAATGAAGAAATATTATTTATAATTGAAGAATATTTTTTTCCATCAAAAATTTACACGGAGGAGATGAAAAGG
1301  AAAAAATAATTGAAAAAGAGACTCCATCCCAAGATATCAACAACAAGATACCATCTCTTCATATGTTTTAAGTATTTAATTTTTTTCAATCTTTTTTT
1401  TTCTCATCTTCTTCTTATTTTAATCATCTAAAAGAAATTATTTATGTTTTTTTTTTAACTTTTAATTATAATATTATCCAGCAGGAGATGATACACAAGAAAT
1501  ACCAAAGATGGAACATCAGGAGGTAACTATATTATCACCCCACTCCCTCCACTACTCATTTAAAAATGACTTATTCATTCATTGATTCAATTATTTATTTAATTCGTTTG
1601  AAATCAAACTAAGGTTACCATATTATCACCCCACTCCCTCCACTACTCATTTAAAAATGATGGTTTGATACATTTGCATGCAATTTGTTTATTCATAAGTC
1701  ATTTATTTTCAAAATTTTATGTTCAGTAAACGTTTGCATACATTTGTTTATACATAATTCATCTATTTCTTTAAAATTTATGTTCAGTTAAACG
1801  ATTGCATACATTTGTTCATACATAAGTCATCTATTTTTTAAAAAAAATTATGTTCAGTTAACGTTTGCATACAATTTTGTCTCATACATAATTCATCT
```

```
2901  AATCTATCAGAAAATACGATAATAAAGAAGTCACCCTGAAAATAAATATTAATTTTGTGACGTGAAAGCAATATCAAGAGCCCCGTCAATTTGTTGTAT  3000
3001  TATGTCAGATGCAACATCCTTCTTTCTCGTCGAAGTAGTAGGAGCGCTTAGCACACATCTCAACATAATGCCCGATAATAACGTTTAATGGTGAATCT  3100
3101  ATCGGTATCATAACAATAGTATACAACTTTAAACCTAATGATCGTCTAGCTAGTAATCTTTCAAAATGAGGACCCTAATTACTGACAAAATTTGTGTCT  3200
3201  AACATAACTTATGTACCATAACAATAATATATCTTGTGTAATTTATGACTGAAGGTAGGGTTTGAAATTAAACATAATCAATAAAATTGGACAAAGAAGA  3300
                                                                              Exon 9
3301  TATTATTTATTGAAAGATATTAATAGTTTTTTTCTTCAAAATTACAGGAAGGAGATGACAAGAGACTCCATCACAAGATATCATCAAGATGGAAG  3400
3401  GTATCAATCTATTTATATTTTTATAAGTATTTTTTCTTACAATTTTTTATTTCCTTTGGTATATATGAAACTATTTTTTTAACCATCTTTAAAAAA  3500
                                              Exon 10
3501  AAATAATAACTTATGTATAACTATAATCATGATATTATCATCCAGGGGACCGTGCCACTAGAAATAACAAAGGTGGTATGTGAGGTAACTAAATTTCTT  3600
3601  CCAATTTTTCTATACATTATGTTTGTATTTTTTTTTGGATTCATTCGAACTTTCTTCGATAGAAGTGTTCCTATCTATATACGATTAAAATTATATT  3700
3701  CAGTTTACGGATAAAAATATATTTAAACAATTCTTTTTAATTTCATATCTAAACTATTGAAAATGTGTCGCCCTCGTAACCTCGGTACAAAGCCAACT  3800
3801  AGAACCACATTTTAAATGATTAAAAAAATCTTTTGAAAGTGTGAGAAATACGGTCGAAACTATCCCTTATTATTTTATTTTACGTATATGCAATAGACAA  3900
3901  TATTGAATCCTCTCTATTTATTCGTATGTTACTTCCTCACATATCAAATCTCTTAGTAAAAATTCTGACTTCACCACTGTATATATCTTTTATTTTG  4000
```

FIGURE 8B2

```
4201 ACGAGAAGATCTTGGTGTTGAATCAAAACCTCCATCAAAGGCTGATCCTCCCAAAATGCAAACAGACAATAATAAACTCTAGAAACATCCAAAAAAATT
4301 AATAATAAAAATTATAATTCAGAACGATAAAGTAAAAATTCTGAATTGTCTCCCGTTAGAAAAGTAACTTCAATAAATATTTGTCTTTCTTTGTAT
4401 TTTCAAAGTGTAATTGGTTATTGTACTTTGAGAAGCTTTCTTTAGATTGTTATGTACTTGTATTGCTTCCTTCTTTTGGCTTATTTATATAATATAAA
4501 TAAAAATAAATAAATATCTAATGAT
             4526
```

FIGURE 8C

```
Ex3  CgAGgAgATG aAAgGAaAA AATAaTTGAA AAAGAGACTC CATCCCAAGA TATCAACAAC AAAGAtaaca tctcttcata tgttttaag
Ex7  GnAGgAtAtG aAAaGAgAA AATAGTTGAA AAAGAGACTC CATCCCAAGA TATCAACAAC AAAG...... :::::::::   :::::::::
Ex5  GgAGgAtATG tAAAgGAgAA AATt.....GAA AgGAGACTa tATCCCAAtA TATCAtCAAg AttGAag...  :::::::::   :::::::::
Ex9  ......... .........gA AggAGaTGAc AAAGAGACTg CATCaCAAGA TATCAtCAAg AtgGAag...  :::::::::   :::::::::
Ex1  ......... :AAA:GA:AA AATAGTTGAA AtgGgaACTC CtTCatAtGA TATCAAaAAC AAAG......  :::::::::   :::::::::
Con  G-:AG-A-ATG -AAA-GA-AA AATAGTTGAA AAAGAGACTC CATCCCAAGA TATCAACAAG AAAGA-----  ---------   ---------
```

FIGURE 11A

```
Ex4  ....AGATGA TaCACAAGAA AtACCAAAGa TGGAACATGA CgAg......
Ex8  ...GAGATGA TGCACAAGAA AAACGAAAGG TGGAACATGA G.........
Ex6  gagatGATGA TGCACAAGAA AAACL.AAGG TtGAgtATGA GgAg......
Ex10 ...GgGAgCg TGCACtAGAA AtAaCAAAGG TGGtAtgTGA G.........
Ex2  ...GAGATGA catgCAAGAA gAACCAAAGG TGaAACtTcA ccAtgagaag
Con  ---GAGATGA TGCACAAGAA AAACCAAAGG TGGAACATGA G-A-------
```

FIGURE 11B

```
         31                                                    40
Rep A    Glu lys glu lys ile ile glu lys glu thr pro ser gln asp ile asn asn lys
         111                                                   120
Rep 2A   Glu lys glu lys ile val glu lys glu thr pro ser gln asp ile asn asn lys 58                                           71
Rep B    Asp asp thr gln glu ile pro lys met glu his glu glu gly
         130                                          143
Rep 2B   Asp asp ala gln glu lys pro lys val glu his glu glu gly 81                                          93
Rep C    Lys glu thr ile ser gln tyr ile ile lys ile glu gly
         146                                         158
Rep 2C   Lys glu thr pro ser gln asp ile ile lys met glu gly
```

FIGURE 12

Exon 3  AAGATACCATCTCTTCATATGTTTTAAG

Exon 7  AAGATATCATATCTTCATATGCCTAAG
            ╱  ╲
          GTAT

FIGURE 14

SYSTEMIN

RELATED APPLICATIONS

The present application claims priority under 35 U.S.C. §120 from PCT International Application No. PCT/US93/02428, filed Mar. 18, 1993, which is a continuation-in-part of U.S. Ser. No. 07/855,412, filed Mar. 19, 1992, now U.S. Pat. No. 5,378,819, which is a continuation-in-part of U.S. Ser. No. 07/528,956, filed May 25, 1990, now abandoned, and a continuation-in-part of PCT International Application No. PCT/US91/03685.

GOVERNMENT SPONSORSHIP

This invention was made with government support under grant number DCB9104542 awarded by the National Science Foundation. The government has certain rights in the invention.

FIELD OF THE INVENTION

This invention relates to methods and materials for inducing plant defense mechanisms. More particularly, this invention relates to methods for inducing the production of plant defense proteins, such as proteinase inhibitors, and to methods of regulating resistance to predators, herbivores, insect, pathogen or virus in plants by inducing or suppressing the expression of genes encoding systemin or prosystemin.

BACKGROUND OF THE INVENTION

Damage to crops by predators (i.e., insects, herbivores, and pathogens, including fungi, bacteria, and viruses), results in substantial annual losses in agricultural production. Man has created and employed a wide range of chemicals in attempting to reduce damage to plant crops. Many environmental problems have been created by the widespread use of chemicals that may only provide a transient level of protection for crops. Chemicals also suffer from the disadvantage that all organisms in an area may be indiscriminately treated, causing needless damage to many beneficial organisms. Many chemicals are also potentially toxic to man and animals.

Attempts to reduce crop damage have included selective breeding for resistance, but resistance traits can frequently be controlled by many genes making it difficult (or impossible) to genetically select a desired attribute. Decreased crop yields are also commonly encountered in resistance strains. Accordingly, there exists a strong need for compositions and processes to improve the resistance of plants under attack by herbivores.

Plants have evolved inducible defensive mechanisms that respond to attacks by predators (C. A. Ryan, 1990, *Ann. Rev. Phytopathol.* 28:425; D. J. Bowles, 1990, *Ann. Rev. Biochem,* 59:873; M. Chessin and A. E. Zipf, 1990, *The Botanical Review* 56:193; D. L. Dreyer and B. C. Campbell, 1987, *Plant, Cell and Environ.* 10:353). One mechanism involves systemic synthesis of serine proteinase inhibitors that are accumulated at distal tissue sites in plants. The proteinases can inhibit the digestive enzymes of insects and microorganisms (T. R. Green and C. A. Ryan, 1972, *Science* 175:776; C. A. Ryan, 1978, *TIBS* 3(7):148; V. A. Hilder, A. M. R. Gatehouse, S. E. Sheerman, R. F. Barker, D. Boulter, 1987 *Nature* 330:160; R. Johnson, J. Narvaez, G. An, C. A. Ryan, 1989, *Proc. Natl. Acad. Sci. U.S.A.* 86:9871). Proteinase inhibitors can be detrimental to the growth and development of insects from a variety of genera including Heliothis, Spodoptera, Diabiotica and Tribolium (Ryan, supra; Broadway, supra; Rechsteiner, supra). Several families of polypeptides have been described that inhibit serine proteinases, including: the Kunitz family (e.g., Soybean trypsin inhibitor); the Bowman-Birk family; (e.g., Soybean proteinase inhibitor); the Potato I and Potato II families; the Barley trypsin inhibitor family; and, the Squash inhibitor family.

Wounding of plants by animals, including insects, and pathogens or mechanical damage reportedly induces transcriptional activation of proteinase inhibitor genes and protein synthesis (J. S. Graham, G. Hall, G. Pearce, C. A. Ryan, 1986, *Planta* 169:399). The latter wound-response has reportedly been described in a variety of species including; tomato (J. S. Graham, G. Pearce, J. Merryweather, K. Titani, L. Ericsson, C. A. Ryan, 1985, *J. Biol. Chem.* 260(11):6555; J. S. Graham, G. Pearce, J. Merryweather, K. Titani, L. H. Ericsson, C. A. Ryan, 1985, *J. Biol. Chem.* 260(11):6561), potato (C. A. Ryan, 1968, *Plant Physiol.* 43:1880), alfalfa (W. E. Brown and C. A. Ryan, 1984, *Biochemistry* 23:3418; W. E. Brown, K. Takio, K. Titani, C. A. Ryan, 1985, *Biochemistry* 24:2105), cucurbits (D. Roby, A. Toppan, M. T. Esquerre-Tugaye, 1987, *Physiol. Mol. Pl. Pathol.* 30:6453) and poplar trees (H. D. Bradshaw, J. B. Hoflick, T. J. Parsons, H. R. G. Clarke, 1989, *Plant Mol. Biol.* 14:51). Wounding reportedly results in the rapid accumulation of proteinase inhibitors not only in wounded leaves but also in distal, unwounded leaves, suggesting that a signal, or signals, released from the wound site travels throughout the plant. Transport of these signals is mediated locally through intercellular and intracellular fluids that permeate wound or infection sites (Green, T. R. and C. A. Ryan, *Science* 35 175:776–777, 1972) or travel systemically through the vascular system of plants (Kuc, J. and C. Presisig, Mycologia 76:767–784,1984: M. Kopp, et al., *Plant Physiol.* 90:208–216, 1990; and K. E. Hammond-Kosack, et al., *Physiol. Mol Plant Path.* 35:495–506, 1989). Proposed wound signals include: pectic fragments derived from the plant cell wall (C. A. Ryan and E. E. Farmer, 1991, *Annu. Rev. Plant. Physiol. Mol. Bio.* 42:651); the lipid-derived molecule, jasmonic acid (E. E. Farmer and C. A. Ryan, 1990, *Proc. Natl. Acad. Sci. U.S.A.* 87:7713); the plant hormone, abscisic acid (H. Pena-Cortes, J. J. Sanchez-Serrano, R. Mertens, L. Willmitzer, S. Prat, 1989, *Proc. Natl. Acad. Sci. U.S.A.* 86:9851); electrical potentials (E. Davies, 1987, *Plant, Cell and Environ.* 10:623; J. F. Thain, H. M. Doherty, D. J. Bowles, D. C. Wildon, 1990, *Plant, Cell and Environ.* 13:569); and, more recently, an 18-amino acid polypeptide called systemin (G. Pearce, D. Strydom, S. Johnson, C. A. Ryan, 1991, *Science* 253:895).

SUMMARY OF THE INVENTION

Disclosed herein are a) the isolation and sequencing of Systemin, an 18-amino acid polypeptide (SEQ ID No.3) and first polypeptide hormone found in plants; b) the isolation and sequencing of prosystemin, a precursor 200 amino acid 23kDa polypeptide(SEQ ID No. 1); c) the molecular cloning of cDNA encoding prosystemin (SEQ ID No. 2) and genomic DNA encoding prosystemin mRNA(SEQ ID No. 4); d) the construction of antisense vectors encoding antisense RNA inhibiting prosystemin synthesis; e) the construction of vectors containing the prosepetemin or systemin sense nucleic acid, as well as, f) a method of enhancing the defense mechanism of plants. Systemin has been shown to be a powerful inducer of the synthesis of wound-inducible plant defense proteins including members of proteinase inhibitor families, i.e., the Inhibitor I(8100 Da) and Inhibitor II(12,300 Da) families. Radioactively labelled systemin applied to a plant wound site is rapidly translocated to distal tissues where it induces synthesis of defense proteins. Systemin is represented only once in the precursor prosystemin molecule and is located close to the carboxy terminus of the precursor protein. Plants expressing antisense prosystemin RNA exhibit a greatly reduced synthesis of wound-induced proteinase inhibitors. Transgenic plants expressing sense prosystemin RNA exhibit an increased level of wound-induced proteinase inhibitors. *Manduca sexta* larvae exhibit lowered growth weight when feeding on transgenic sense tomato plants compared to those larvae feeding on wild type plants.

Nucleic acid sequences of the invention are capable of encoding a systemin or prosystemin polypeptide or antisense RNA. The nucleic acids comprise a nucleotide sequence capable of hybridizing with the sense or antisense strand of the nucleotide sequence of the prosystemin cDNA (SEQ ID No. 2) or genomic DNA(SEQ ID No. 4). The nucleic acids of the invention encode prosystemin and systemin polypeptides or are antisense sequences which interfere with the expression of systemin or prosystemin in vivo. Systemin related polypeptides of the present invention comprise the amino acid sequence $R_1R_1QR_1R_2PPR_1R_2R_2R_1PPR_2R_1QR_1R_1$, wherein $R_1$ is any amino acid, $R_2$ is lysine or arginine (or any derivative thereof), Q is glutamine (or any derivative thereof), and P is proline (or any derivative thereof. A representative example of a systemin polypeptide of the invention is the amino acid sequence: $NH_3$-AVQSKPPSKRDPPKMQTD-COO-(SEQ ID No. 3).

The processes of the present invention are useful for enhancing synthesis of defense proteins in a plant by introducing a prosystemin sense nucleic acid into a plant cell, or inhibiting synthesis by introducing an antisense nucleic acid. Transgenic plants containing the subject nucleic acids of the invention are also provided.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 3 shows the amino acid sequence of the systemin polypeptide(SEQ ID No. 3).

FIG. 5A shows the autoradiograph of a tomato leaf that was treated with $^{14}$C-labeled synthetic systemin polypeptide to demonstrate transport of systemin from wound sites into distal plant tissues.

FIG. 5B shows the $^{14}$C-labeled synthetic systemin isolated by reverse-phase HPLC from the distal plant tissues of FIG. 5A.

FIG. 6 shows the amino acid sequence of prosystemin (SEQ ID No. 1).

FIGS. 7A and 7B show the nucleotide sequence of cDNA encoding prosystemin (SEQ ID No. 2) with crosshatched underlining showing repeated sequence motifs and vertical bar underlining showing the location of systemin in the precursor sequence.

FIGS. 8A1 and 8A2 show the nucleotide sequence of the prosystemin gene from position 1 to position 2100 (SEQ ID No. 4).

FIGS. 8B1 and 8B2 show the nucleotide sequence of the prosystemin gene from position 2101 to position 4200 (SEQ ID No. 4).

FIG. 8C shows the nucleotide sequence of the prosystemin gene from position 4201 to position 4526 (SEQ ID No. 4).

FIG. 11 shows sequence alignment of the prosystemin gene exons. The consensus sequence (con) is composed of those bases that occur at the same position in at least three of the five exon sequences.

FIGS. 11A shows the alignment of sequences of the first exons of each pair(exon 3, bases 1285–1373 of SEQ ID No. 4; exon 7, bases 2442–2505 of SEQ ID No. 4; exon 5, bases 2051–2117 of SEQ ID No. 4; exon 9, bases 3352–3400 of SEQ ID No. 4; exon 1, bases 105–138 of SEQ ID No. 4; and, con, SEQ ID No. 5).

FIGS. 11B shows the alignment of the sequences of the second exons of each pair (exon 4, bases 1483–1522 of SEQ ID No. 4; exon 8, bases 2672–2709 of SEQ ID No. 4; exon 6, bases 2275–2318 of SEQ ID No. 4; exon 10, bases 3545–3582 of SEQ ID No. 4; exon 2, bases 286–332 of SEQ ID No. 4; and, con, SEQ ID No. 6) .

FIG. 12 shows sequence alignment of three repeated polypeptide sequences within prosystemin (SEQ ID No.1). Three polypeptide sequences (Rep A, Rep B and Rep C; each occurring once within the amino-terminal half of prosystemin), are aligned with the homologous sequences (Rep 2A, Rep 2B and Rep 2C; each occurring once within the carboxy terminal half of prosystemin). Amino acids which differ between repeats are underlined. The amino acids at the beginning and end of each repeat are numbered from the amino terminus of prosystemin.

FIG. 14 shows a sequence comparison of the intron boundary at the 3'-end of the exons 3 (SEQ ID No.7) and 7 (SEQ ID No. 8). Exon sequence is underlined. The first four bases of the intron at the 3'-end of exon 7 have been displaced to facilitate accurate alignment of the homologous sequences occurring at the 3'-end of exon 3 and at the 5'-end of the intron between exons 7 and 8.

DETAILED DESCRIPTION OF THE PREFERRED EMBODIMENT

Figure 1:
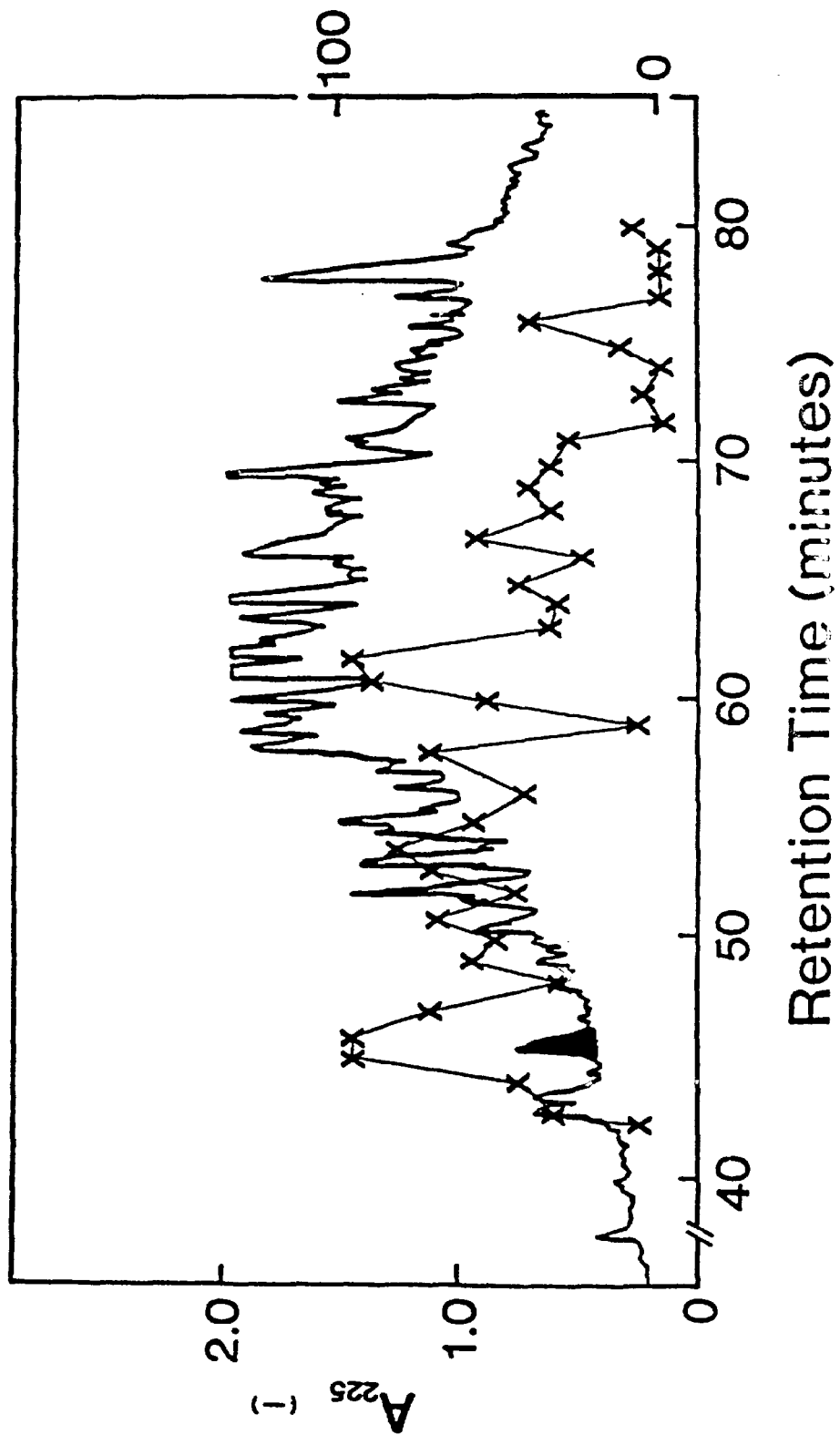
FIG. 1 shows preliminary purification of systemin from the extracts of tomato leaves by semipreparative reverse-phase HPLC as described in Example 1, below.

As used herein the following terms are used to mean:

The term "defense proteins" is intended to include proteins that impede plant tissue attack or ingestion by predators, such as by herbivores, insects, fungi, bacteria or viruses. Defense proteins increase resistance of plants to predator attack by acting directly to impede plant tissue attack or ingestion, or by acting indirectly to produce other defense compounds from precursor materials, (e.g., by acting to induce enzymes in a pathway synthesizing defense compounds; or, by inducing proteins that regulate enzymes that synthesize defense compounds). Representative examples of defense proteins include: e.g., proteinase inhibitors, thionins, chitinases and β-glucanases. Representative enzymes that lead to the synthesis of defense compounds include, e.g., casbene synthase. Representative enzymes that are part of a biosynthetic pathway leading to synthesis of defense compounds includes, e.g. enzymes in the phenylpropenoid and terpenoid pathways for synthesis of phytoalexin antibiotics, alkaloids and other toxic chemicals. Other predator defense proteins useful in connection with the invention disclosed herein will, of course, be apparent to those skilled in the art. Particularly suitable predator defense proteins include inhibitors of digestive proteolytic enzymes of the attacking herbivore, such as proteinase inhibitors, and antibacterial, antimycotic, and antiviral compounds and the like. Representative proteinase inhibitor defense proteins include, e.g., the Kunitz family of trypsin inhibitors, the Bowman-Birk family of proteinase inhibitors, the Inhibitor I family of proteinase inhibitors, the Inhibitor II family of proteinase inhibitors, the barley family of trypsin inhibitors, and the squash family of proteinase inhibitors. Representative examples of plant proteinase inhibitors are disclosed in PCT/US/91/03685, a continuation-in-part application of U.S. patent application Ser. No. 07/528,956, the disclosures of both applications are incorporated herein by reference.

The term "nucleic acid" is intended to mean natural and synthetic linear and sequential arrays of nucleotides and nucleosides, e.g., in cDNA, genomic DNA (gDNA), mRNA, and RNA, oligonucleotides, oligonucleosides, and derivatives thereof. For ease of discussion, such nucleic acids are at times collectively referred to herein as "constructs," "plasmids," or "vectors." Representative examples of the nucleic acids of the invention include bacterial plasmid vectors such as expression, cosmid, and cloning and transformation vectors (e.g., pBR322, λ, Ti, and the like), plant viral vectors (e.g., modified CaMV and the like), and synthetic oligonucleotide molecules such as chemically synthesized RNA or DNA.

The term "encoding" is intended to mean that the subject nucleic acid may be transcribed and translated into the subject protein in a cell, e.g., when the subject nucleic acid is linked to appropriate control sequences such as promoter and enhancer elements in a suitable vector (e.g., an expression vector) and when the vector is introduced into a cell.

The term "polypeptide" is used to mean three or more amino acids linked in a serial array.

The term "antisense DNA" is used to mean a gene sequence DNA that has a nucleotide sequence homologous with the "sense strand" of a gene when read in a reversed orientation, i.e., DNA read into RNA in a 3' to 5' rather than 5' to 3' direction. The term "antisense RNA" is used to mean a RNA nucleotide sequence (e.g., encoded by an antisense DNA or synthesized complementary with said antisense DNA). Antisense RNA is capable of hybridizing under stringent conditions with an antisense DNA. The antisense RNA of the invention is useful for inhibiting expression of a "target gene" either at the transcriptional or translational level. For example, transcription of the subject nucleic acids may produce antisense transcripts that are capable of inhibiting transcription by inhibiting initiation of transcription or by competing for limiting transcription factors; or, the antisense transcripts may inhibit transport of the "target RNA"; or, the antisense transcripts may inhibit translation of "target RNA".

The term "sense strand" is used to mean the single stranded DNA molecule from a genomic DNA that is transcribable and translatable into the polypeptide product of the gene. The term "antisense strand" is used to mean the single strand DNA molecule of a genomic DNA that is complementary with the sense strand of the gene.

The term "capable of hybridizing under stringent conditions" is used to mean annealing a first nucleic acid to a second nucleic acid under stringent conditions (defined below). For example, the first nucleic acid may be a test sample, and the second nucleic acid may be the sense or antisense strand of a prosystemin gene. Hybridization of the first and second nucleic acids is conducted under stringent conditions, e.g., high temperature and/or low salt content, which tend to disfavor hybridization of dissimilar nucleotide sequences. A suitable protocol involving hybridization in 6 X SSC, at 42° C. in aqueous solution followed by washing with 1 X SSC, at 55° C. in aqueous solution is provided in the illustrative examples below. (Other experimental conditions for controlling stringency are described in Maniatis, T., et al., *Molecular Cloning; A Laboratory Manual,* Cold Springs Harbor Laboratory, Cold Springs, N.Y., 1982, at pages 387–389; and also in Sambrook, Fritsch, and Maniatis, *Molecular Cloning; A Laboratory Manual, Second Edition,* Volume 2, Cold Springs Harbor Laboratory, Cold Springs, N.Y., 1989, pages 8.46–8.47.)

The term "fragment" when used herein with reference to nucleic acid (e.g., cDNA, genomic DNA, i.e., gDNA) is used to mean a portion of the subject nucleic acid such as constructed artificially (e.g., through chemical synthesis) or by cleaving a natural product into a multiplicity of pieces (e.g., with a nuclease or endonuclease to obtain restriction fragments).

The term "synthetic oligonucleotide" refers to an artificial nucleic acid (e.g., a chemically synthesized nucleic acid) having 9 or more nucleotides.

The term "systemin polypeptide" is used to mean a polypeptide having an amino acid sequence $R_1R_1QR_1R_2PPR_1R_2R_2R_1PPR_2R_1QR_1\ R_1$, wherein $R_1$ is any amino acid, $R_2$ is lysine or arginine (or derivative thereof, Q is glutamine (or derivative thereof), and P is proline (or any other derivative thereof), e.g., the systemin polypeptide of FIG. 3; namely, $NH_3$-AVQSKPPSKRDPPKMQTD-COO- (SEQ ID No. 3). Skilled artisans will recognize that through the process of mutation and/or evolution, polypeptides of different lengths, e.g., with insertions, substitutions, deletions, and the like, may have arisen that are related to the systemin polypeptide of the invention by virtue of: a) amino acid and/or nucleotide sequence homology; b) a defensive function in regulating gene expression in response to predators, pathogens, and mechanical injury; and/or, c) the organization of the genomic DNA, as described in Example 6, below. Representative examples of systemin family members in tomato and potato are provided in Example 6–9 (below), and illustrative methods for identification of systemin family members in other species, genra, and families of plants are also provided in Examples 6–9 (below).

The term "systemin nucleic acid" is used herein to refer to that subset of nucleic acids capable of encoding a systemin polypeptide.

The term "prosystemin polypeptide" is used to mean a precursor polypeptide capable of giving rise to a systemin polypeptide. A representative example is provided by the prosystemin polypeptide encoded by the cDNA of FIGS. 7A and 7B (SEQ ID No. 2) or the coding region of the genomic DNA of FIGS. 8A1, 8A2, 8B1, 8B2 and 8C (SEQ ID No. 4). Prosystemin polypeptide is capable of being cleaved (e.g., chemically or enzymatically) to give rise to systemin. A representative method for identifying prosystemin genes in different species of plants is provided in Example 9, below.

The term "prosystemin nucleic acid" is used herein to refer to that subset of nucleic acids capable of encoding a prosystemin polypeptide.

Embodiments of the invention described and illustrated below provide systemin and prosystemin polypeptides, nucleic acids encoding systemin and prosystemin mRNA, cDNA, and genomic DNA, and, including 5' regulatory sequences controlling transcription of prosystemin gDNA into mRNA. The subject nucleic acids of the invention are capable of encoding prosystemins that are constitutively synthesized at a low level and wound-inducible to a high level (see illustrative Example 7, below). Would-inducible and constitutive low-level expression is provided by regulatory elements within 3000 bp of the 5' region of the systemin gene sequence, the first 104 nucleotides of which are shown in FIG. 8A (SEQ ID No. 4). Promoter, enhancer, and other regulatory elements within the 3000 bp 5' region are useful for insertion into recombinant plasmids and vectors for controlling gene expression in plants, (i.e., genes other than prosystemin). Representative examples of genes that may be linked to the 5' regulatory elements of prosystemin include; genes encoding storage or nutritionally important proteins, such as vegetative storage proteins, seed storage proteins, tuber storage proteins and the like; and, genes encoding other plant defense genes, i.e., other proteinase inhibitors Bt toxen, and the like; genes encoding regulatory enzymes for metabolic and defensive processes, including phenylalanine amines, HMG CIA reductase and the like; genes encoding commercially important enzymes in plant syspension culture, such as proteinases, lipases, and the like; and, genes that regulate flower color.

Purification and physical properties of a representative systemin polypeptide are disclosed (Example 1, below). Skilled artisans will recognize that the relatively high proportion of hydrophilic amino acids in the prosystemin polypeptide suggest a variety of conventional approaches to purification that may be used to purify a natural, recombinant, or synthetic prosystemin polypeptide, (e.g., ion exchange chromatography, affinity chromatography, specific ion precipitation, and the like).

The subject amino acid sequence of prosystemin disclosed herein provides amino acid sequences that may be used to construct synthetic peptides of prosystemin or systemin; or, alternatively they may be used to instruct sites at which cleavage of a prosystemin polypeptide will liberate a systemin (e.g., enzymatic cleavage sites in a natural prosystemin or a chimeric recombinant prosystemin protein. In the latter case a chimeric recombinant prosystemin polypeptide may be produced in an expression system, the chimeric protein purified, and then systemin liberated from the chimeric protein by enzymatic cleavage.). Cleaving a prosystemin polypeptide at boundary amino acids produces systemin, e.g., cleaving the prosystemin of FIG. 7B (SEQ ID No. 2) at both $Leu_{178}$-$Ala_{179}$, (e.g., cleaving with an Leu-Ala-specific endopeptidase; abbreviated, LA peptidase) and at $Asp_{196}$-$Asn_{197}$ (e.g., cleaving with an Asp-Asn-specific endopeptidase; abbreviated, DN peptidase). As an alternative to the LA peptidase, a prosystemin polypeptide may also be cleaved by suitable enzymes at other upstream sites such as $Arg_{175}$-$Glu_{176}$ or $Glu_{176}$-$Asp_{177}$; followed by sequential cleavage of the product with an N-terminal peptidase, i.e., until the LA residues are reached and cleaved. In a similar manner and as an alternative to a DN peptidase, a carboxypeptidase or carboxydipeptidase may be used to sequentially remote amino acids, from the carboxy-terminus until the DN residues are reached and cleaved. Those skilled in the art will recognize that a suitable LA-specific peptidase(s) may be isolated from plant tissues, e.g., by using natural (or synthetic) polypeptide substrates having the prosystemin-systemin boundary amino acid sequences (e.g., L-A and D-N) and assaying for the production of systemin biological activity. In one such illustrative example, a recombinant prosystemin chimeric protein may be synthesized by an expression system and used as a substrate in enzymatic assays to identify and isolate the LA and/or DN peptidase(s).

Those skilled in the art will recognize that the subject prosystemin amino acid sequence may be used for constructing proteinase inhibitors specific for the LA and/or DN peptidases, and such inhibitors may be useful for inhibiting systemin production from prosystemin; thereby inhibiting systemin activation of defense protein production in plants. Skilled artisans will also recognize that LA and DN peptidase may be selected with enhanced ability to liberate systemin from prosystemin (e.g. LA and DN enzymes having increased turnover number, decreased Km, increased Vmax, or decreased sensitivity to feedback inhibition, and the like). Strains of plants may either be selected, or constructed (i.e., as transgenic plants), having increased LA and/or DN peptidase activity. The subject plants may exhibit increased resistance to predators.

The subject systemin polypeptides of the present invention may also be used for identifying and isolating systemin receptors from plant cells. Those skilled in the art will recognize that the subject polypeptides can be labeled (e.g., with a radioactive label) and conjugated to a photochemical crosslinking agent. The subject conjugated and radiolabeled polypeptides bind to the cellular systemin receptor and photochemical activation forms covalent bonds between the polypeptide and its receptor. When the receptor-polypeptide complex is extracted from the cell it may be isolated and identified by virtue of its label, e.g., the molecular size may be conveniently determined by SDS-PAGE and autoradiography. The subject polypeptides of the invention may also be useful in ligand affinity chromatography for isolating systemin receptors.

Embodiments of the invention provide processes for enhancing or inhibiting synthesis of a defense protein in a plant by introducing the subject nucleic acids of the invention into a plant cell. In one representative example enhanced defense protein production may be achieved by inserting prosystemin (or systemin) nucleic acid in a vector downstream from a promoter sequence capable of driving constitutive high-level expression in a plant cell. In the latter case, when the subject vector is introduced into a plant cell the cells containing one or more copies of the subject nucleic acid may exhibit increased synthesis of systemin. When grown into plants the transgenic plants may exhibit increased synthesis of defense proteins, and increased resistance to herbivores, as discussed in more detail in Example 11, below.

In another embodiment, the invention provides processes for inhibiting synthesis of defense proteins in a plant by inserting prosystemin antisense nucleic acid in a vector downstream from a promoter sequence. When the latter construct is introduced into plant cells the cells containing one or more copies of the subject nucleic acid may exhibit decreased synthesis of defense proteins. A representative example of a prosystemin antisense vector, and process for inhibiting synthesis of defense proteins is provided in Example 10, below.

Transgenic plants containing the subject antisense nucleic acids of the invention are useful for: a) identifying other mediators that may be present in the prosystemin molecule, (e.g., other mediators that may induce expression of defense proteins or differentiation); b) establishing the extent to which any specific insect and/or pathogen is responsible for damage of a particular plant. In the latter case the transgenic plants of the invention are useful for assessing the importance of systemin defense mechanisms in production of a plant as a crop.

In still other embodiments, the invention provides transgenic plants constructed by introducing a subject nucleic acid of the invention into a plant cell, and growing the cell into a callus and then into a plant; or, alternatively by breeding a transgenic plant from the subject process with a second plant to form an F1 or higher hybrid (i.e., F2). The subject transgenic plants and progeny may be used to find those plants that contain extra copies of the subject nucleic acid of the invention, and increased expression of prosystemin or systemin. A representative example of a process for producing such a transgenic plant, and breeding it to obtain F1 offspring is provided below in Example 10.

Those skilled in the art will recognize the agricultural advantages inherent in plants constructed to have either increased or decreased expression of systemin polypeptide. For example, such plants may have increased resistance to attack by predators, insects, pathogens, microorganisms, herbivores, mechanical damage and the like. Skilled artisans will also recognize that chemical agents may be developed that will mimic or induce systemin activity (e.g., in a manner similar to methyl jasmonate induction of systemin activity), and these chemical agents may be useful when sprayed on plants in maximizing crop resistance to herbivores, pathogens, and mechanical damage. Representative examples of plants in which the process may be useful include (but are not limited to) tomato, potato, tobacco, corn, wheat, rice, cotton, soybean, alfalfa, rape, poplar trees, pine and fir trees and the like.

The subject nucleic acids of the invention are also useful as oligonucleotide probes (e.g., $^{32}$P-labeled synthetic oligonucleotides constructed to complement portions of prosystemin nucleotide sequence), and restriction fragment probes (e.g., end-labeled restriction fragments of prosystemin cDNA), in Northern and Southern blots for selecting and screening among plants to find natural and mutant strains with increased prosystemin expression and/or genomic copy number. This screening procedure can be useful for identifying plant strains with increased resistance to attack by predators, herbivores, insects, bacteria, fungi, viruses, mechanical damage, and the like.

The subject polypeptides of the invention are useful for inducing monoclonal and polyclonal antibodies that may be used in immunoassays to detect the presence or amount of a prosystemin or systemin polypeptide in plant tissues, extracts, and fluids (e.g. see E. Harlow and D. Lane, *Antibodies: A Laboratory Manual,* Cold Springs Harbor Laboratory, Cold Springs, N.Y. 1988). The latter immunoassays may prove useful for identifying natural and mutant strains of plants with increased levels of prosystemin or systemin. Strains exhibiting increased levels of the subject polypeptides may have increased resistance to attack by herbivores, i.e., insects, bacteria, fungi, and viruses.

Systemin is a primary polypeptide signal mediating wound-inducible expression of defense genes in distal leaves and, therefore, is the first example of a peptide hormone found in plants. The expression of a recombinant antisense genetic expression construct (i.e., containing an antisense prosystemin cDNA) resulted in an almost complete suppression of systemic wound induced defense protein synthesis in plants. The latter finding provides evidence that systemin is an integral component of the systemic signal transduction system in plants that induces defense protein synthesis in response to attack by predators and the like. It is considered most likely that systemin is the first member to be identified in a systemin family of plant polypeptide hormones. It is considered highly likely that members of the systemin family may regulate developmental events in the meristems, flower tissues, and fruit of plants, e.g., tomatoes and potatoes. Other members of the systemin family may be identified by virtue of their amino acid or nucleotide sequence homology with prosystemin or systemin, or by their ability to hybridize with the subject prosystemin or systemin nucleic acids of the invention. (In this regard, the nucleotide sequences of the exons identified in Example 6, below, may prove useful as oligonucleotide probes for identifying other systemin family members.) In this case the ability of a DNA or RNA to hybridize with the nucleic acid of the invention under conditions of reduced stringency, (e.g., a suitable protocol involving hybridization in 6 X SSC, at 42° C. in aqueous solution followed by washing with 1 X SSC, at 55° C. in aqueous solution) will be considered a preliminary indication that the DNA or RNA contains a systemin family member. The DNA or RNA may then be sequenced and the sequence compared with the sequence of systemin and prosystemin. (Experimental conditions for controlling stringency are also described in Maniatis, T., et al., *Molecular Cloning; A Laboratory Manual,* Cold Springs Harbor Laboratory, Cold Springs, N.Y., 1982, at pages 387–389; and, also in Sambrook, Fritsch, and Maniatis, *Molecular Cloning; A Laboratory Manual, Second Edition,* Volume 2, Cold Springs Harbor Laboratory, Cold Springs, N.Y., 1989, pages 8.46–8.47.) Systemin family members may be recognized by virtue of about 50% to about 100%, or more preferably about 70% to about 100%, and most preferably about 80% to about 100% homology at the amino acid or nucleotide level, i.e., over a stretch of about 5 or more amino acids or about 15 or more nucleotides.

The foregoing may be appreciated more fully by reference to the following representative examples of the subject compositions and methods provided by the invention.

EXAMPLE 1

Isolation and Sequencing of the Systemin Polypeptide

Oligogalacturonides were initially considered to be primary candidates as systemic signals for the wound response because they elicit synthesis of antibiotic phytoalexins in plant cells near the sites of infections (10, 11). Oligogalacturonides are released by pectin-degrading that are not found in tomato leaves. In addition, when labeled α-1,4-oligogalacturonides were applied to wound sites on tomato plants, they were not found to be mobile (E. A. -H. Baydoun and S. Fry, *Planta* 165, 269 1985). Thus, oligogalacturonides are probably not involved as systemic mediators of signal transduction in plants, at least with respect to induction of proteinase inhibitor genes in response to wounding.

A search was initiated for systemic signals inducing proteinase Inhibitor I and II genes in tomato leaf extracts. This search led us to identify a polypeptide in tomato leaves that is free of carbohydrates and induces proteinase inhibitor activity when supplied to young tomato plants. The polypeptide was purified using high-performance liquid chromatography (HPLC, see Materials and Methods, below). Inducing activity of the polypeptide was assayed by cutting the petioles of young plants and introducing eluted fractions from column separations into the cut over a period of 30 min. The plants were subsequently transferred to small vials of water, incubated under constant light for 24 hours as described (C. A. Ryan, *Plant Physiol.* 54, 328, 1974), and the amount of proteinase Inhibitor I and II in the leaf juice was quantified by radial immunodiffusion in agar gels that contained rabbit antiserum to Inhibitor I or Inhibitor II (C. A. Ryan, *Anal. Biochem.* 19, 434, 1967; R. Trautman, K. Cowan, G. Wagner, *Immunochemistry* 8, 901, 1971). Over 30,000 young tomato plants were assayed over a 2.5 year period. With the use of this protocol, slightly more than 1 µg of an active factor (i.e., systemin) was isolated from approximately 60 pounds of tomato leaves.

The elution profile of the preliminary extract of tomato leaves (FIG. 1) was complex. Several fractions exhibited proteinase inhibitor inducing activity but one peak (FIG. 1) was selected for further purification because it contained the highest activity and the best yield from the purification.

Figure 2:
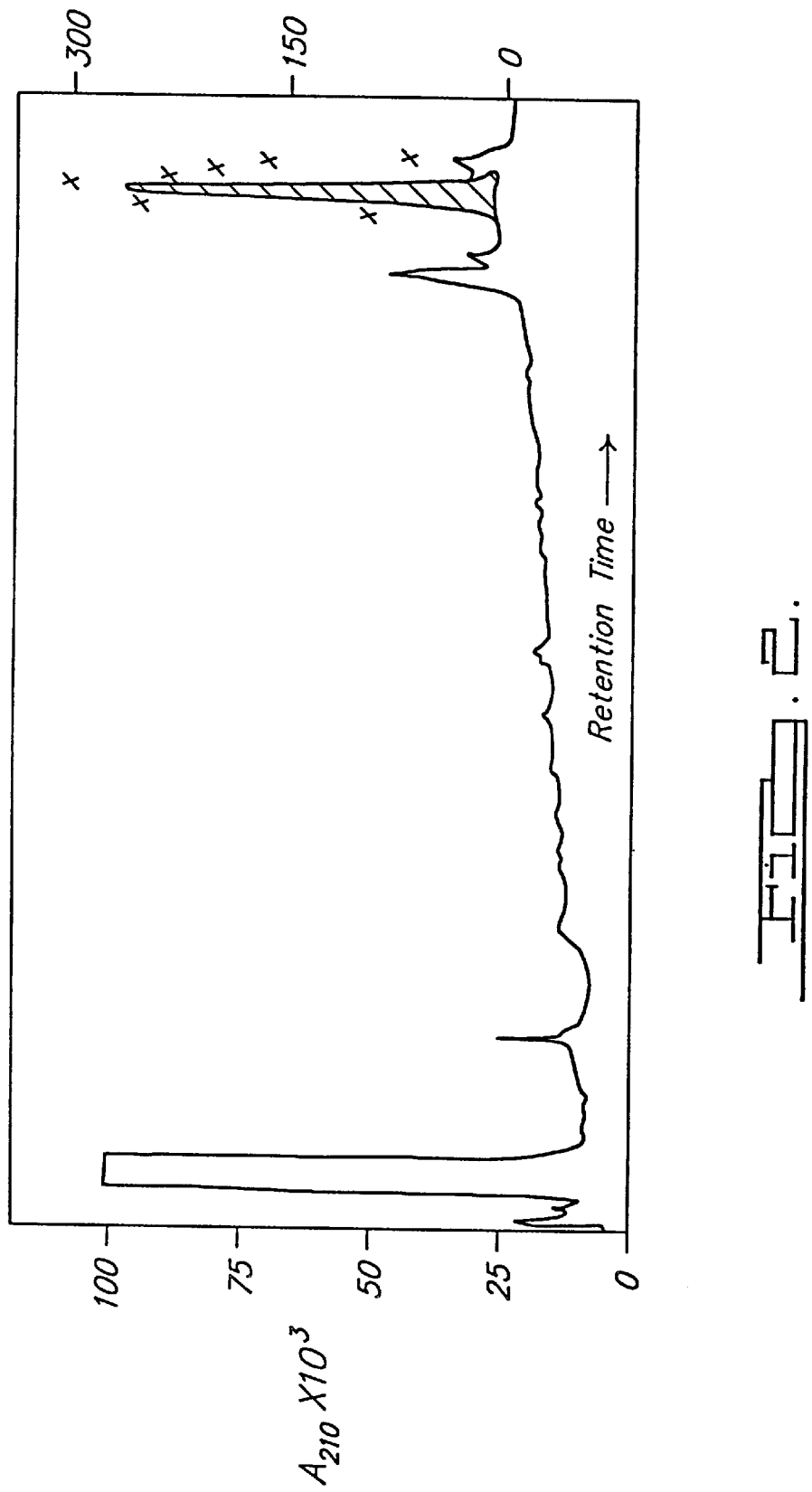
FIG. 2 shows substantial purification of systemin by chromatography on an SCX-HPLC column as described in Example 1, below.

After several additional purification steps (see Materials and Methods, below), a major peak that possessed high specific activity was eluted from a strong cation exchange (SCX) HPLC column (FIG. 2). The properties of the eluted material resembled those of a polypeptide, that is, absorbance in the spectral region appropriate for peptide bonds, total loss of activity and recovery of free amino acids after acid hydrolysis, partial loss of activity in the presence of trypsin and other proteolytic enzymes, and a positive assay result with bicinchoninic acid (P. K. Smith et al., *Anal. Biochem.* 150, 76, 1985). Total amino acid analysis of the bioactive peak eluted from the SCX-HPLC (step 5, Materials and Methods, below) was determined as described below. The amino acid sequence analysis of the active component (conducted as described below; see, Materials and Methods) identified its length and determined the sequence of FIG. 3: $NH_3$-AVQSKPPSKRDPPKMQTQTD-COO- (SEQ ID No. 3)). No significant similarities were found to known protein sequences and the polypeptide was named "systemin" (Protein Identification Resource release 26; Pearson/Lipman FASTA program at the Molecular Biology Computer Research Resource, Harvard Medical School). The sequence is a palindrome: xxQxBPPxBBxP-PBxQxx (x, any amino acid residue; B, Lys or Arg; Q, Gln; P, Pro). A synthesized polypeptide of identical sequence to the systemin sequence (prepared as described below; see, Materials and Methods) eluted from the C18 (step 2) column with the same retention time as the native polypeptide.

Materials and Methods:

Purification and isolation of the polypeptide inducer of defense proteins:

Step 1: Approximately 2 kg of tomato leaves *Lycopersicon esculentum* (v. Castlemart) were harvested from 20-day-old plants, grown under cycles of 17 hours light at 28° C. and 7 hours dark at 18° C. Leaves were homogenized in a Waring blender for 5 min with distilled water (total volume of 4 liters) and filtered through four layers of cheesecloth. The liquid was adjusted to pH 4.5 with HCl and centrifuged at 1000 g for 10 min. The supernatant was adjusted to pH 6.1 with 10N NaOH, centrifuged at 10,000 g for 10 min at 20° C., and decanted through Whatman #4 filter paper. The filtrate was chromatographed on DEAE cellulose, followed by reversed-phase C18 flash chromatography, Sephadex G25 gel filtration, and then CM Sephadex chromatography.

The DEAE cellulose column (Whatman DE52, 5.9 cm by 15 cm) was equilibrated in 1M ammonium bicarbonate and washed exhaustively with distilled water. The material eluting in the void volume was collected and stored overnight at 4° C. TFA was added dropwise to the stored elute to a final concentration of 0.2% (v/v); the solution was then clarified by centrifugation at 20,000 g for 5 min at room temperature. The supernatant was loaded onto a reversed-phase flash column (C18, 40 μm, 3 cm by 25 cm) previously equilibrated with aqueous 0.1% TFA. The column was eluted with the use of compressed nitrogen at 8 psi. After the sample was loaded, the column was washed with 200 ml 0.1% TFA; the retained material was then eluted with successive washes of 20, 40, and 60% methanol in 0.1% TFA. The methanol was removed with a rotary evaporator and the remaining liquid was frozen and lyophilized. Two kilograms of leaf material yielded about 1 g of crude material containing systemin. The procedure was repeated 15 times. Samples (approximately 4 g) of crude material dissolved in 20 ml water and adjusted to pH 7.8 with 10M ammonium hydroxide were loaded onto a G25 Sephadex column (4 cm by 44 cm) that was equilibrated with 50 mM ammonium bicarbonate, pH 7.8. The material eluting at and just after the void volume was recovered and lyophilized. Four identical runs through the entire procedure produced 1.25 g of partially purified systemin. The 1.25 g was dissolved in 500 ml $H_2O$, the pH was adjusted to 6 with 1M NaOH, and the sample was applied to a CM Sephadex column (2 cm by 17 cm) and washed with 0.01M potassium phosphate, pH 6. The activity was retained by the CM Sephadex, eluted with 250 mM ammonium bicarbonate, and lyophilized. The total yield of proteins in this step was 190 mg.

Step 2: The active fraction (190 mg) recovered from step 1 was dissolved in 10 ml 0.1% TFA, centrifuged at 20,000 g for 5 min, filtered, and chromatographed on a reversed-phase C18 column. Five microliters of each 2-ml eluted fraction was diluted to 360 μl with 154 mM sodium phosphate, pH 6.5, and assayed for proteinase Inhibitor I inducing activity (x in FIG. 1). Four plants were assayed per fraction. The material was injected into a semi-preparative reversed-phase C18 column (Vydac, Hesperia, CA, Column 218 TP510, 10 mm by 250 mm, 5-μm beads, 300A pores). Solvent A consisted of 0.1% TFA in water. Solvent B consisted of 0.1% TFA in acetonitrile. Samples were injected in solvent A and, after 2 min, a 90 minute gradient to 30% solvent B was begun for elution. The flow rate was 2 ml/min and eluted peaks were monitored at 225 nm. Several peaks of biological activity were found (as described below). The major peak of activity (shown in black in FIG. 1) resided in tubes 43 to 46, which were pooled and lyophilized. Total protein content of the pooled factions was estimated at 2.5 mg.

Step 3: The total material recovered in step 2, above (2.5 mg), was subjected to strong cation exchange HPLC on a poly-SULFO-ETHYL Aspartamide (SCX) column (4.6 mm by 200 mm, 5 μm, The Nest Group, Southborough, Me.) with the use of the following solvent systems: Solvent A, 5 mM potassium phosphate, pH 3, in 25% acetronitrile; solvent B, 5 mM potassium phosphate, 500 mM potassium chloride in 25% acetonitrile, pH 3. The sample was dissolved in 2 ml of solvent A, filtered, and applied to the column. After a 5-minute wash with solvent A, a 60-min gradient to 50% B was applied. The flow rate was 1 ml/min, and the elution profile was monitored by absorbance at 210 nm. The active fractions, tubes 35 to 38, were pooled and reduced in volume to 1 ml by vacuum centrifugation.

Step 4: The pooled fractions from step 3 were subjected to reverse-phase C18 HPLC in 10 mM potassium phosphate, pH 6. Chromatography was performed on a Beckman Ultrasphere Ion pair column (4.6 mm by 250 mm, C18, 5 μm).

Solvent A was 10 mM potassium phosphate, pH 6, and solvent B was 10 mM potassium phosphate, pH 6, containing 50% acetonitrile. The active fractions, tubes 39 to 42, were pooled and vacuum centrifuged to a final volume of 1 ml. This fraction was applied to the same column as the previous run but under the solvent and gradient conditions of step 2. The sample was adjusted to pH 3 with TFA, filtered through a 0.45-μm syringe filter and chomatographed at a flow rate of 1 ml/min. The peaks of protein were detected at 212 nm. The fractions containing activity, eluting at 53.5 to 56.5 min, were pooled and vacuum centrifuged to a volume of 1 ml.

Step 5: The active fraction from step 4 was subjected to SCX-HPLC with the same column and conditions as used in step 3, except that the gradient was shallower, i.e., the column was run at 0% B for 5 min at which time a gradient to 30% B in 120 min was started. Fractions (0.5 ml) were diluted as in FIG. 1 and assayed for proteinase Inhibitor I inducing activity (x in FIG. 2). The biologically active fractions of the system peak (shown in black in FIG. 2) were collected and analyzed for amino acid content and sequence. The profile was detected by absorbance at 210 nm. Fractions eluting at 76 to 78.5 min were pooled and vacuum centrifuged to reduce the volume to I ml.

Step 6: The step 5 fraction was desalted on a C18 HPLC column under the conditions of step 2. A 60-minute gradient to 30% solvent B was employed. The fractions containing the activity peak eluted at 55.0 to 58.0 min and were pooled and concentrated by vacuum centrifugation to 0.5 ml. The sample contained approximately 1 μg of protein, as estimated by amino acid content after acid hydrolysis. The biological activity of the sample had the potential to induce maximal accumulation of proteinase inhibitors in 40,000 tomato plants, (i.e., approximately 40,000-fold purified). This sample was used for amino acid analysis and sequence determination.

Amino acid analysis:

The bioactive peak eluted from the SCX-HPLC column (step 6) was dried in 6 by 50 mm glass tubes and hydrolyzed in the HCl vapor. The hydrolysates were derivatized with phenylisothiocyanate and analyzed by reverse-phase chromatography on 30 cm by 0.39 cm columns (Picotag, Millipore) according to the manufacturer's suggestions.

Amino acid sequence analysis:

The amino acid sequence of the bioactive peak-eluted from the SCX-HPLC column (step 6) was determined by established methods (D. J. Strydom et al., *Biochemistry* 25, 945, 1985; B. A. Bidlingmeyer, S. A. Cohen, T. L. Tarvin, *J. Chromatogr.* 336, 93, 1984). Briefly, sequencing was performed on a Beckman model 890 spinning cup instrument, equipped for microsequencing, as recommended by the manufacturer, except that 0.1% water was added to the anhydrous heptafluorobutyric acid (HFBA) and 0.1% ethanethiol was added to the 25% trifluoracetic acid (TFA). Identification of the phenylthiohydantoin amino acids was by reverse-phase chromatography on an octadecylsilane column (IBM, Inc.; 30 cm by 0.46 cm, 3-μm particle size) with the use of the gradient system described (D. J. Styrdom et al., supra). Abbreviations for the amino acid residues are: A, Ala; C, Cys; D, Asp; E, Glu; F, Phe; G, Gly; H, His; I, Iie; K, Lys; L, Leu; M, Met; N, Asn; P, Pro; Q, Gln; R, Arg; S, Ser; T, Thr; V, Val; W, Trp; and Y, Tyr.

Synthesis of a synthetic systemin polypeptide:

A polypeptide corresponding to residues 2 through 18 (FIG. 3; SEQ ID No. 3) was synthesized with the use of 9-fluorenylmethyl chloroformate (F-moc) solid phase chemistry with an Applied Biosystems Inc. Model 431A synthesizer on a p-methyl benzyhyrylamine resin according to the manufacturer's protocol. The F-moc derivative of [$^{14}$C] Ala (New England Nuclear) was synthesized (J. Stewart and J. Young, *Solid Phase Peptide Synthesis* (Pierce Chemical Co., Rockford, Ill., ed. 2, 1984), pp.67–68) and added to the NH$_2$— terminal residue of the polypeptide; the [$^{14}$C] Ala-polypeptide was then cleaved from the resin. The radioactive peptide was purified by C18 HPLC. The specific activity of the synthetic systemin polypeptide was 19.0 $\mu$Ci/$\mu$mol.

EXAMPLE 2

Systemic Translocation of Radiolabeled Systemin Polypeptide

Figure 4:
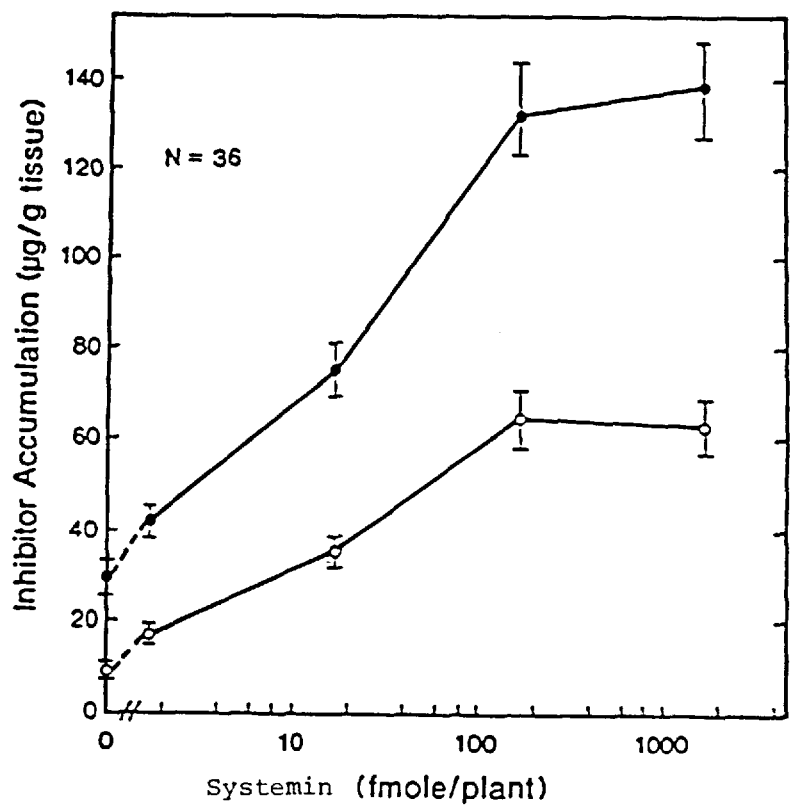
FIG. 4 shows induction of defense protein synthesis, i.e., Inhibitor I (closed circles) and Inhibitor II (open circles), in tomato plants by a synthetic systemin polypeptide, as described in Example 2, below.

The synthetic systemin polypeptide (described above) was tested for bioactivity and was found to be as effective as the native systemin polypeptide (purified above to step 6) for inducing the synthesis and accumulation of both Inhibitor I and II proteins when supplied to the cut stems of young tomato plants (FIG. 4). About 40 fmol of the polypeptide per plant was required to produce half maximal accumulation of Inhibitors I and II, which represents about $10^5$ times more activity on a molar basis than the previously reported PIIF oligogalactunonide inducers derived from plant cell walls. The coordinate induction of synthesis of Inhibitor I and Inhibitor II proteins in response to the systemin synthetic polypeptide (FIG. 4) is similar to a normal plant wound response that is transcriptionally regulated. This suggests that the polypeptide is activating the same signal transduction pathway activated by wounding (T. Green and C. A. Ryan, 1972, supra; J. S. Graham et al., 1986, supra), by oligosaccharides (P. Bishop et al., 1981, supra; M. Walker-Simmons et al., 1983, supra), and by methyl jasmonate (E. E. Farmer et al., 1990, supra).

The systemin polypeptide, unlike the prior reported oligogalacturonides, is transported out of wounds to distal tissues. $^{14}$C-labeled polypeptide was synthesized (as described above, Example 1) and placed on fresh wounds of tomato plants. Within 30 min the radioactivity had moved throughout the leaf, and within 1 to 2 hours radiolabeled systemin was identified by HPLC (FIG. 5) in the phloem exudate (expressed from the plant according to the method described by R. W. King and J. A. ZeeVaart, *Plant Physiol.* 53, 96, 1974). The polypeptide was named "systemin" because of its mobility through phloem.

As well as being inducible by wounding in leaves, the genus for proteinase Inhibitors I and II are developmentally regulated in the meristems, flower tissues, and fruit of tomato species, and in potato tubers. Thus, it is likely that these developmental events may be mediated by systemin or by similar polypeptides that are members of the systemin family.

FIG. 4 shows the results of experiments in which systemin synthetic polypeptides inducted synthesis and accumulation of proteinase Inhibitor I (•) and II (O) in the excised leaves of young tomato plants. The leaves were incubated in solutions containing the synthetic systemin polypeptide and the proteinase inhibitors were assayed as described above in Example 1. Each data point was obtained from assays of the leaves of 36 tomato plants.

EXAMPLE 3

Molecular Cloning Prosystemin

A prosystemin cDNA was isolated by screening a primary cDNA library synthesized from tomato leaf mRNA as follows:

Poly A+ mRNA was purified from tomato leaves using oligo dT columns (Pharmacia). cDNA was synthesized using the Stratagene cDNA synthesis system and was cloned into lambda ZAP vector arms (Stratagene). Approximately 80,000 primary library recombinants were screened, by duplicate plaque lifts, using a degenerate oligonucleotide probe, termed "SP1", based on the amino acid sequence of the carboxy terminus of systemin (i.e. PPKMQTN; amino acids 190 to 196, as numbered in FIG. 6, excluding the last nucleotide residue of the Asp$_{196}$ codon). The hybridization conditions for screening were: 6X SSC; 1X Denhardts solution; 100 $\mu$g/ml, yeast tRNA; 0.5% sodium pyrophosphate and approximately 4×10$^7$ cpm of $^{32}$P-end-labeled SP1. Hybridization was at 37° C. for 36 hr. The filters were washed in several changes of 5X SSC, 0.1% SDS at 48° C. for one hour. Approximately 50 positive clones were identified and rescreened using a second degenerate oligonucleotide, termed "SP2", corresponding to the amino terminus of systemin (AVQSKP; amino acids 179 to 184, as numbered in FIG. 6, excluding the last of the Pro$_{184}$ codon). The hybridization and wash conditions were identical to those used for SP1 except that the wash temperature for SP2 was 40° C. Of the initial positive clones only one hybridized to the SP2 probe. Fragments of the prosystemin cDNA, termed "pSYS 1", were subcloned into Bluescript® plasmids, single-stranded DNA was rescued and sequenced on both strands by dideoxy sequencing using Sequenase (USB; Sanger et al. *PNAS* 73, 5463, 1977). Sequencing of the SP2 positive clone established that it encoded the systemin polypeptide within the larger protein which was called "prosystemin". The prosystemin cDNA was not full-length, beginning at nucleotide 112 as numbered in FIG. 6 and SEQ ID No. 1.

The prosystemin cDNA (SEQ ID No. 2) consisted of 839 bp with an open reading frame encoding 197 amino acids. The reading frame remained open to the 5'-end of the clone, and since Northern blot analysis indicated that the systemin mRNA was 1 Kb in size, we concluded that the cDNA was missing approximately 100 bp at the 5'-end. The complete prosystemin mRNA sequence was subsequently determined by sequencing the prosystemin gene (as described below in Example 6) and mapping the transcriptional start site (FIGS. 7A and 7B; Example 6). The experiments described in Example 6, below, established the length of the open reading frame as 600 base pairs encoding a prosystemin protein of 200 amino acids. The identification of the initiating methionine codon was made on the basis of two criteria; the presence of multiple stop codons immediately 5' to the methionine codon and the presence of an adjacent sequence similar to the plant consensus sequence for translational initiation (H. A. Lutcke et al., 1987, *EMBO Journal* 6:43).

EXAMPLE 4

Structure and Properties of Prosystemin

Based on the cDNA sequence (FIGS. 7A and 7B; SEQ ID No. 2), systemin is located close to the carboxy terminus of the 23 kDa prosystemin protein (FIGS. 7A and 7B; SEQ ID No. 2), amino acid residues 179 to 196; corresponding to nucleotides 639 to 699). The amino acid composition of prosystemin is unusual in that it contains a high percentage of charged amino acids; aspartic acid (10%), glutamic acid (17%), lysine (15%), but very few hydrophobic amino acids. In consequence, prosystemin is a markedly hydrophilic molecule. Analysis of the prosystemin sequence failed to reveal a hydrophobic region at the amino terminus that resembles a leader peptide. The post-translational processing pathway and site of sub-cellular compartmentalization of prosystemin remain to be determined. A search of the EMBL and GeneBank data base, with both the cDNA and deduced protein precursor sequences failed to reveal significant homology to any of the listed sequences.

Although the 18-amino acid systemin sequence occurs only once within the precursor, close to the carboxy terminus, other sequence elements are repeated. There is a short (6 to 9 amino acids), imperfect repeat occurring five times within the prosystemin sequence (crosshatched underlining, FIGS. 7A and 7B). This observation suggests that at least part of the prosystemin gene may have evolved by multiple gene duplication/elongation events, a conclusion which is supported by the structure of the gene.

EXAMPLE 5

Proteolytic Processing Sites in Prosystemin

The putative processing sites bordering systemin are shown in FIGS. 7A and 7B; SEQ ID No. 2 (i.e. amino acid residues 178 and 197). The Leu (178) and Asn (197) processing sites do not conform to the consensus sequence for the endoproteolytic processing sites flanking bioactive peptides within animal prohormone precursors (e.g., see animal sites in R. B. Harris, 1989, *Arch. Biochem. Biophys.* 275(2):315 (1989). The minimum animal consensus sequence consists of a pair of basic amino acids which immediately precede the site of cleavage. In addition, the dibasic pair is often preceded, at a distance of two or three amino acids, by a single basic amino acid. The animal consensus sequence is, however, found once within the prosystemin sequence, at residues 183–188 (LysProProSerLysArg, FIGS. 7A and 7B; SEQ ID No. 2), which is a part of the mature systemin polypeptide. It is conceivable that the half-life of systemin is regulated by further processing at this site, e.g., to yield an 8 amino acid carboxy-terminal peptide.

In animal systems prohormones are often processed to yield multiple bioactive peptides (J. Douglass, O. Civelli and E. Herbert, 1984, *Ann. Rev. Biochem.* 53:665; L. J. Jung and R. H. Schefler, 1991, *Science* 251:1330) and members of the systemin family of plant polypeptide hormones may be subject to similar processing mechanisms.

EXAMPLE 6

Structure of the Prosystemin Gene and Systemin Gene Family

A primary library of 700,000 recombinants was plated on the bacterial strain (P2) PLK-17 (Stratagene) and screened, by duplicate plaque lifts, with nick-translated prosystemin cDNA. Hybridization was carried out as described below. A single positive clone was identified and purified. The gene was located on a 18 Kb genomic DNA fragment from which it was sub-cloned into Bluescript® plasmids. A series of overlapping, deletions spanning most of the gene were produced using the Mung Bean/Exonuclease III system (Stratagene). Each deletion product was cloned into a Bluescript® phagemid from which single-stranded DNA was rescued for use as the sequencing template. The gene was sequenced by the dideoxy method of Sanger (supra) using Sequenase (U.S.B.). The sequence was completed using custom-made oligonucleotide primers. The deduced sequence was then confirmed using custom-made oligonucleotide primers (as described in the Materials and Methods below).

Figures 9A, 9B, 9C:
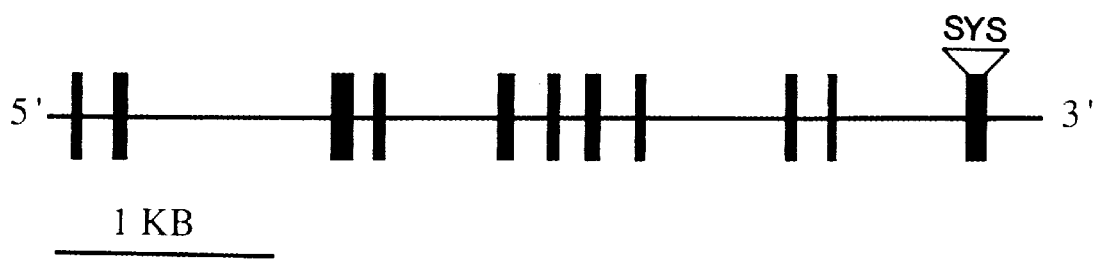
FIG. 9A shows the organization of the prosystemin gene. The gene consists of a 104 bp 5'-untranslated region, a 4176 bp coding region composed of 11 exons (vertical bars) interrupted by 10 introns, and a 246 bp 3'-untranslated region. The position of systemin is indicated by a horizontal bar labelled SYS.
FIG. 9B shows a Southern blot analysis of the prosystemin gene. Tomato genomic DNA was isolated from leaves (as described in Example 6, below), and 5 µg was digested with EcoRI (lane 1); Bg1 II (lane 2) or Sca I (lane 3), and electrophoresed on a 0.8% agarose gel that was probed with nick-translated prosystemin.
FIG. 9C shows a Southern blot analysis of the species distribution of prosystemin gene homologues, as described in Example 9, below. Genomic DNA (5 µg) from tomato (lane 1), potato (lane 2), tobacco (lane 3), alfalfa (lane 4), and Arabidopsis (lane 5) was digested with EcoRI and electrophoresed on a 0.8% agarose gel. The gel was blotted onto nitrocellulose and probed with nick-translated prosystemin cDNA.

The sequence of the prosystemin gene is presented in FIGS. 8A1–8C and SEQ ID No. 4. The gene is composed of 4526 bp comprising a 104 bp 5'-untranslated region, a 4176 bp coding region and a 246 bp 3'-untranslated region. A striking feature of the sequence is that it is 76% A:T-rich. The structure of the prosystemin gene is depicted in FIG. 9A; Southern blot analysis is shown in FIG. 9B.

Figure 10:
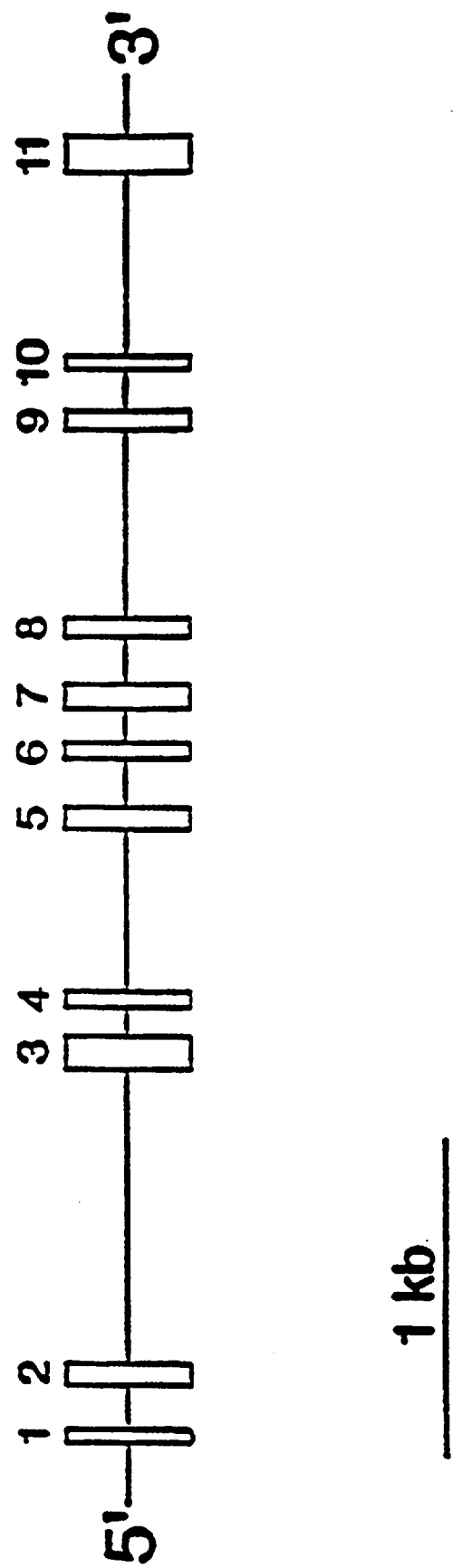
FIG. 10 shows the organization of the prosystemin gene. Exons are represented by vertical bars and numbered 1 to 11. The five exon pairs are: 1 plus 2; 3 plus 4; 5 plus 6; 7 plus 8 and 9 plus 10.

Within the prosystemin gene ten introns interrupt the coding region (FIG. 10). in consequence, the exons are small, ranging, in size from 34 bp (exon 1) to 90 bp (exon 10). The first 10 exons are organized as five pairs while the sequence encoding systemin is located on the final, unpaired exon. To investigate the relationship between the exon pairs we aligned the sequences of the first exon of each pair (exons 1, 3, 5, 7, 9) and, separately, we aligned the sequences of the second exon of each pair (exons 2, 4, 6, 8, 10), as shown in FIGS. 11A AND 11B (also SEQ ID Nos. 4, 5 and 6). The sequences within the first exon group are all homologous to each other as are the sequences within the second exon group. There is no significant sequence homology between the two groups. These observations suggest that the five exon pairs arose by successive duplications from a common ancestor. That the individual exons within a pair are not homologous to each other suggests that the ancestral unit from which the gene is derived was a structure corresponding to the exon pair rather than to the individual exons within a pair.

In contrast to the set of five homologous exon pairs, the exon encoding systemin (exon 11) does not show significant sequence homology with any other part of the prosystemin gene. This observation suggests either that the exon encoding systemin may have arisen separately from the rest of the gene, to which it was subsequently added, or that the exon encoding systemin arose from the same ancestral sequence as the other exons but subsequently evolved more rapidly. Repeated amino acid sequences within prosystemin and the systemin gene family.

The amino acid sequence of prosystemin, like that of the gene, is highly repetitive. A short oligopeptide sequence palendrome was identified above in systemin (Example 1) and a similar theme occurring five times within prosystemin that is encoded by the first exon of each of the five homologue pairs. In addition, the presence of three different, tandemly-repeated polypeptide elements within prosystemin provides a clue about the evolution of the prosystemin gene.

Figure 13A:
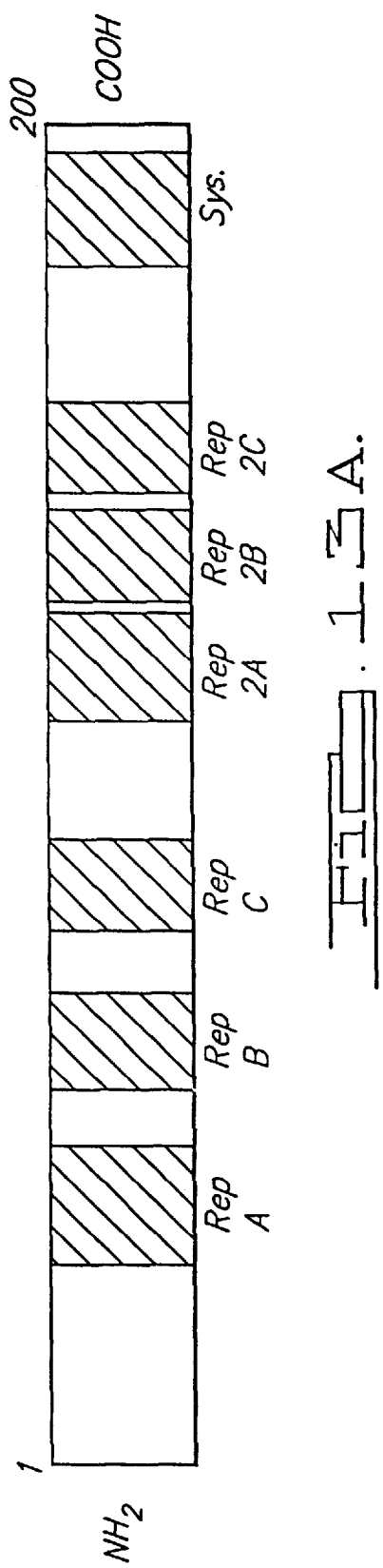
FIG. 13A shows the positions of the duplicated polypeptide sequences within prosystemin. Prosystemin is represented by a horizontal bar with the amino acid residues numbered 1 to 200 from the amino terminus. Sequence elements Rep A, Rep B and Rep C and their repeats Rep 2A, Rep 2B and Rep 2C are indicated by hatched bars. Systemin is represented by a hatched bar labelled Sys.
Figure 13B:
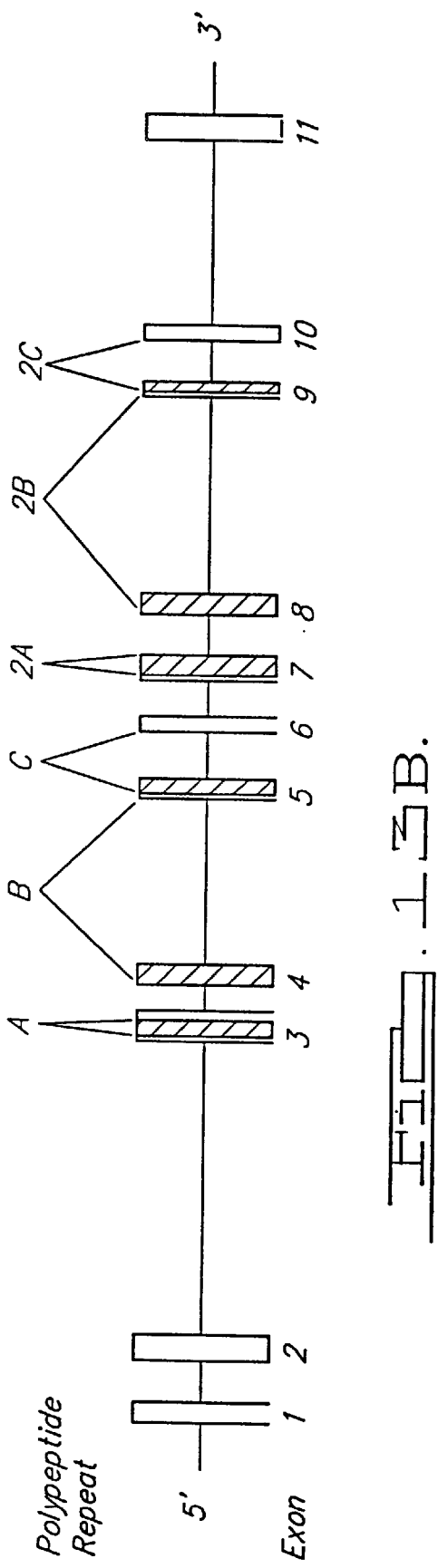
FIG. 13B shows the location of the sequences encoding the polypeptide repeats within the prosystemin gene. Exons are represented by vertical bars. The parts of the exons encoding the polypeptide repeats are shaded.

The tandemly repeated elements occur once within the amino-terminal half of prosystemin and once within the carboxy-terminal half of prosystemin. The polypeptide elements within the amino-terminal half of the precursor have been labelled Rep A, Rep B and Rep C and their repeats within the carboxy-terminal half of the molecule have been labelled Rep 2A, Rep 2B and Rep 2C. The sequences of these repeated polypeptide elements are shown aligned in FIG. 12. The locations of the repeats within prosystemin are shown in FIG. 13A, while the locations within the prosystemin gene of the DNA sequences encoding the polypeptide repeats are shown in FIG. 13B. As can be seen from this comparison the Rep a, Rep B and Rep C polypeptides are encoded by two exon pairs (namely, three plus four and five plus six) while Rep 2A, Rep 2B and Rep 2C are also encoded by two other exon pairs (namely, seven plus eight and nine plus ten).

The observations thus suggest that a set of polypeptide sequences, encoded by two pairs of exons, has been duplicated as one step in the evolution of the prosystemin gene. It would then appear that the ancestral gene for prosystemin was subject to a tandem duplication of a structure composed of at least two pairs of exons. This conclusion precludes a model in which the systemin gene evolved simply by successive duplications of a single exon pair.

Intron boundaries may be shifted within repeated DNA sequences.

The amino acid sequences between the polypeptide Rep A, Rep B and Rep C regions, that was found in the amino terminal half of prosystemin, were not duplicated in the carboxy terminal half of the molecule where repeats Rep 2A, Rep 2B and Rep 2C are almost contiguous (FIG. 13A). This observation is largely explained by the fact that exon 7 (encoding element Rep 2A), is truncated at its 3'-end (i.e., with respect to the sequence of exon 3, encoding element Rep A). Similarly, exon 9 (encoding element Rep 2C), is truncated at its 5'-end (i.e., compared to exon 5, encoding element Rep C).

In the case of exon 7, the truncation did not arise by deleting a short section of the gene, but by shifting the position of the intron boundary within the existing sequence. Comparing the sequence around the intron junction at the 3'-end of exon 7 with the corresponding junction sequence at the 3'-end of exon 3 (FIG. 14; SEQ ID Nos. 6 and 7), it is evident that the sequence corresponding to the 3'-end of the exon 3 constitutes the 5'-end of the intron between exons 7 and 8. This structure may have arisen by either the elongation of exon 3 or the shortening of exon 7. It is not clear if the same process resulted in the truncation of the 5'-end of exon 9.

Materials and Methods:

Primer extension was performed using a gel-purified oligonucleotide consisting of bases 82 to 111 of the antisense strand of the cDNA sequence shown in FIGS. 7A and 7B (SEQ ID No. 2). Total RNA was extracted from young tomato plants 4 hr after wounding and poly A+ mRNA was isolated using oligo dT columns (Pharmacia). Three picomoles of oligonucleotide were end-labelled using γ-ATP at a specific activity of 6000/Ci/mmol. $2 \times 10^6$ cpm of labelled oligonucleotide were annealed to 4 µg polyA+ mRNA by heating to 85° C. for 10 min then hybridizing overnight at 30° C. in a solution of 40 mM PIPES, pH 6.4; 1 mM EDTA; 0.4 M NaCl; 80% formamide. The annealed nucleic acids were ethanol precipitated and resuspended in 30 µl of a solution containing: 50 mM Tris, pH 7.5; 75 mM KCI; 10 mM dithiothreitol; 3 mM $MgCl_2$; 500 µM of each dNTP; 100 µg/ml bovine serum albumin. Thirty units of M-MLV Reverse Transcriptase (Stratagene) and one unit of RNase Block II (Stratagene) were added and the reaction mixture was incubated for 90 min at 37° C. At the end of the reaction one µl of 0.5M EDTA, pH 8.0 and one µl of DNAse-free RNAse A (10 mg/ml) were added to the reaction mixture and incubated for a further 30 min at 37° C. The reaction mixture was phenol extracted, ethanol precipitated and resuspended in four µl TE buffer (10 mM Tric-HCL, pH 7.5, 0.1 mM EDTA, pH 8.0) to which six µl of formamide loading buffer (80% formamide; 10 mM EDTA, pH 8.0; 1 mg/ml xylene cyanol; 1 mg/ml bromophenol blue) were subsequently added. Two µl of the resuspended products were analyzed on a 6% acrylamide/8M urea sequencing gel. The size standards were sequencing products generated using the primer extension oligonucleotide as primer and single-stranded DNA derived from the 5'-end of the prosystemin gene as template. Sequencing was carried out using Sequenase (USB) following the manufacturer's instructions for generating sequencing products close to the primer.

Mung Bean Nuclease analysis was carried out using a 400 bp Scal-Ndel fragment spanning the 5'-end of the prosystemin gene. The Ndel site is located within the first exon of the systemin gene. The Ndel end of the fragment was end-labelled to a specific activity of $6 \times 10^6$ cpm/µg and approximately $10^6$ cpm were mixed with 4 µg of the same poly A+ RNA stock used in the primer extension experiment. The mixture was desiccated and resuspended in 15 µl of hybridization buffer. The mixture was covered with mineral oil, heated to 82° C. for 6 min then hybridized overnight at 37° C. The sample was then mixed with 200 µl of ice-cold Mung Bean Nuclease buffer (30 mM sodium acetate (pH 5.0), 50 mM sodium chloride, I mM zinc chloride, 5% (v/v) glycerol) to which 10 units of Mung Bean Nuclease (Stratagene) were added. The mixture was incubated for 30 min at 12° C. then extracted with an equal volume of a 1:1 mixture of phenol:chloroform. The digestion products were coprecipitated with 1 µg of yeast tRNA and resuspended in 4 µl TE buffer plus 6 µl formamide loading buffer. Three µl of the resuspended digestion products were analyzed on a 6% acrylamide/8M urea gel. Size markers were generated by using single-stranded DNA corresponding to the 5'-end of the gene as template. The sequencing primer was a 19-mer corresponding to the first 19 bases (antisense strand) at the 3'-end of the Scal-Ndel probe fragment.

EXAMPLE 7

Wound-Inducible Expression of the Prosystemin Gene

Figure 15A:
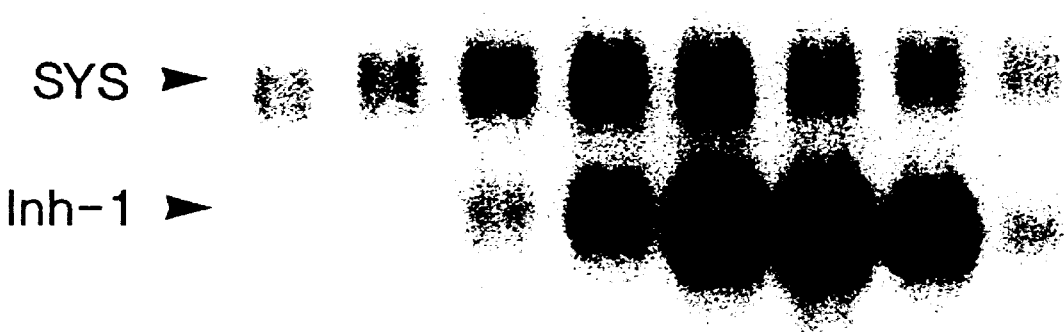
FIG. 15A shows a Northern blot analysis of the time course of induction of prosystemin mRNA and Inhibitor I mRNA after wounding, as described in Example 7, below.

In considering the role of systemin as a mobile signal that activates proteinase inhibitor genes in response to wounding, we investigated the possibility that the prosystemin gene, itself, might be wound-inducible. Northern blot analysis was used to examine the levels of prosystemin mRNA and Inhibitor I mRNA in leaves of unwounded and wounded tomato plants (FIG. 15A). Thirty-two young tomato plants were wounded three weeks after germination. The plants had an upper and a lower leaf and a small apial leaf. The lower leaf was wounded and mRNA was isolated from the upper (unwounded) leaf at the following time points after wounding: 0.5, 1.5, 3, 6, 9, 12, and 24 hours. Four plants were used for each time point. Total RNA (5 µg) from each time point was electrophoresed on a 1.4% agarose-formaldehyde gel and blotted onto nitrocellulose. The blot was probed simultaneously with nick-translated prosystemin (SYS) and Inhibitor I (Inh-1) cDNAs (see Materials and Methods, below). Prosystemin mRNA was found to accumulate in both wounded and unwounded leaves of wounded tomato plants, demonstrating that prosystemin mRNA, like Inhibitor I mRNA, is systemically wound-inducible. Prosystemin mRNA reached the highest levels at three to four hours after wounding while Inhibitor I mRNA was most abundant eight to ten hours after wounding. Unlike the proteinase Inhibitor I message, which is absent in the leaves of unwounded tomato plants, a low level of prosystemin mRNA was detected in the leaves of unwounded plants. Low, constitutive expression of the prosystemin gene in leaves may provide a continuous supply of systemin, allowing the plant to immediately respond to wounding.

The wound-induced accumulation of prosystemin mRNA and, presumably, prosystemin and systemin in the unwounded tissue may amplify the ability of the plant to react to subsequent damage. Continued damage by insect attacks would, therefore, liberate more systemin from the newly synthesized precursor than did the initial wounds, resulting in higher levels of proteinase inhibitor synthesis as the attacks persist.

Since the initial rate of accumulation of prosystemin mRNA was faster than that of Inhibitor I mRNA in response to wounding (FIG. 15A), some aspects of the signal transduction pathways activating the two genes may differ. Additional signals may be responsible for the different rates of accumulation or the signal transduction pathways may respond to the same signals but with different sensitivities.
Materials and Methods:

Nick-translation was performed using the NEN DuPont nick-translation system according to the manufacturer's instructions. Hybridization was carried out under the following conditions: 50% formamide; 5X Denhardts; 5X SSPE; 0.1% SDS; 100 µg/ml sheared salmon sperm DNA; 1 µg/ml poly A and nick-translated DNA probe of specific activity approximately $10^9$ cpm/µg. Unless otherwise stated, blots were washed in 1 X SSC, 0.1% SDS at 65° C.

EXAMPLE 8

Distribution of Prosystemin mRNA Throughout the Plant

Figure 15B:
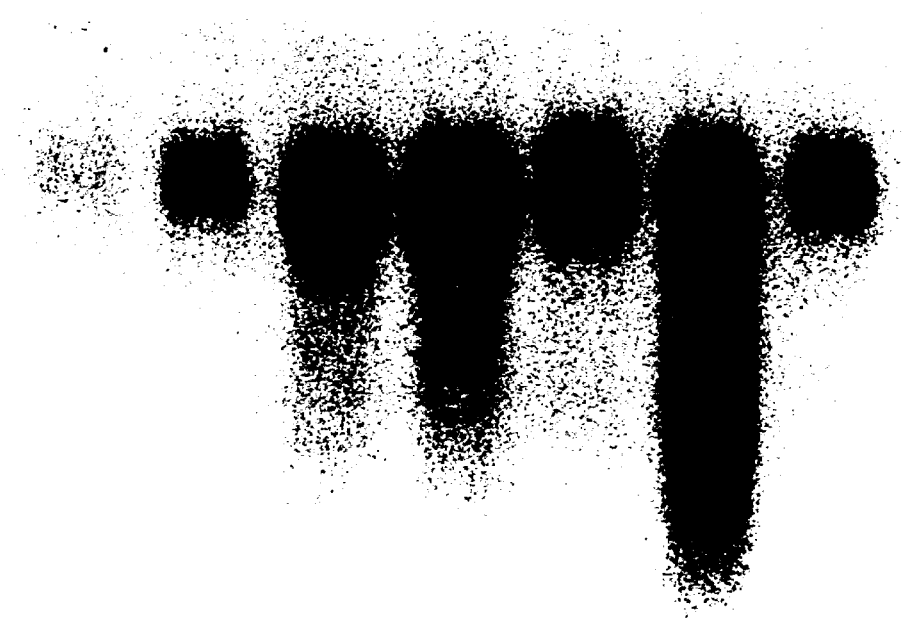
FIG. 15B shows a Northern blot analysis of the distribution of prosystemin mRNA in various parts of an unwounded, fully-grown tomato plant, as described in Example 8, below. Total RNA was extracted from the following parts of an unwounded tomato plant; root (R); stem (St); petiole (Pt); leaf (Le); sepal (Se); petal (Pe); stamen (Sm) and pistil (Pi).

Prosystemin mRNA is found throughout the aerial parts of the plant but not in the roots (FIG. 15B). Total RNA was extracted from the following parts of an unwounded, fully-grown tomato plant: root (R); stem (St); petiole (Pt), leaf (Le), sepal (Se), petal (Pe), stamen (Sm) and pistil (Pi)(FIG. 15B). Total RNA (5 µg) from each sample was electrophoresed and blotted as described in Example 7. The blot was probed with nick-translated prosystemin cDNA (as described in Example 7, above).

The highest constitutive levels of prosystemin mRNA are seen in the flower parts, a feature which is also characteristic of the distribution of Inhibitor I and Inhibitor II mRNAs. The general distribution of prosystemin mRNA (at least in the parts of the plant above ground), is consistent with the proposed role of systemin as a wound signal, since wounding of any aerial part of the plant would be expected to result in the systemic induction of proteinase inhibitor synthesis. The apparent absence of prosystemin mRNA in the roots is surprising since we have observed the induction of proteinase inhibitor synthesis in tomato leaves in response to wounding of the roots. It is possible that roots either contain very low levels of prosystemin mRNA, undetectable in the assay, or they employ a different wound signal(s) (e.g., a different systemin gene family member) to activate proteinase inhibitor genes in the leaves. It is also conceivable that prosystemin is transported from leaves to roots where systemin is released in response to wounding.

EXAMPLE 9

Species Distribution of Prosystemin Gene Homologues

To determine if prosystemin gene homologues are found in other plant species, Southern and Northern blot analysis was performed on genomic DNA and total RNA from three species known to possess wound-inducible proteinase inhibitors: potato, *Solanum tuberosum*, var. Russett Burbank (C. A. Ryan, 1968, *Plant Physiol.* 43, 1880), tobacco, *Nicotiana tabacum*, var. Xanthi (G. Pearce, results in preparation), and alfalfa, *Medicago sativa*, var. Vernema (W. E. Brown and C. A. Ryan, 1984, *Biochemistry* 23:3418; W. E. Brown, K. Takio, K. Titani, C. A. Ryan, 1985, *Biochemistry* 24:2105); and, as a control, from one species (*Arabidopsis thaliana*, var. Columbia), which is not known to possess wound-inducible proteinase inhibitors.

Southern blot analysis of the species distribution of prosystemin gene homologues is shown in FIG. 9C. Genomic DNA (5 µg) from tomato (FIG. 9C, lane 1), potato (FIG. 9C, lane 2), tobacco (FIG. 9C, lane 3), alfalfa (FIG. 9C, lane 4), and Arabidopsis (FIG. 9C, lane 5) was digested with EcoRI; restriction fragments were separated by electrophoresis on a 0.8% agarose gel; and, fragments of prosystemin were visualized by blotting to nitrocellulose and probing with nick-translated prosystemin cDNA. The blot was washed at 55° C. under moderately stringent conditions. Of the four plant species analyzed, a homologue of the prosystemin gene was identified under moderately stringent conditions only in potato (the nearest relative of the four species to tomato). A potato mRNA species was also identified that hybridized to tomato prosystemin cDNA and which comigrated with the tomato prosystemin mRNA. The nucleotide sequence of the gene in tobacco, alfalfa and Arabidopsis may have diverged from that of the tomato gene to the extent that it can no longer be detected by hybridization under stringent conditions with the tomato prosystemin cDNA. This interpretation is favored by the findings that a homologue could not be detected at greatly reduced hybridization and wash stringencies. Analysis of extracts from other plant genera should provide further insights into the distribution and evolution of members of the systemin gene family.

EXAMPLE 10

Antisense Suppresion of the Prosystemin Gene.

To determine if the prosystemin gene product has an important role in the systemic signal transduction leading to the expression of proteinase inhibitor genes in tomato leaves, a prosystemin antisense DNA was constructed and was used to transform tomato plants. The chimeric antisense DNA was composed of prosystemin cDNA, in the antisense 3' to 5' orientation, under the control of the constitutive CaMV 35S promoter and inserted into the binary vector pGA643.
Materials and Methods:

Strand-specific, radiolabeled RNA probes were produced from the prosystemin cDNA using T3 and T7 RNA polymerases (Stratagene) according to the manufacturer's instructions.

The antisense DNA construct was transformed into Agrobacterium strain LBA4404 and the recombinant bacteria were used to transform tomato var. Better Boy. As controls for the primary transformants, tomato plants were transformed with the binary vector alone. Eighteen antisense plants and twenty one controls were regenerated. Three weeks after the transformed plants had been transferred to soil the lower leaves on each plant were extensively wounded and the levels of wound-inducible proteinase Inhibitors I and II were determined in the expressed juice of upper leaves twenty four hours later (C. A. Ryan, 1967, *Anal. Biochem.* 19:434; R. Trautman, K. M. Cown, G. G. Wagner, 1971, *Immunochemistry* 8:901). None of the plants were producing either Inhibitor I or Inhibitor II in their leaves prior to wounding. Of the 18 plants containing the antisense gene, 11 plants produced Inhibitor I at less than 40% of the mean control level of 126.7+/−18.6 µg/ml leaf juice and Inhibitor II at less than 30% of the mean control level of 164.7+/−18.6 µg/ml leaf juice.

Figure 16A:
FIG. 16A shows a Northern blot analysis of total RNA extracted from transgenic antisense plant 1A4. Lane 1 shows the results obtained with the sense probe and Lane 2 shows the results with the antisense probe, as described in Example 10, below.

FIG. 16A shows Northern blot analysis of total RNA isolated from one of the antisense plants, designated 1A4, using both sense and antisense-specific single-stranded RNA probes. Two samples of total RNA (5 µg) were electrophoresed and blotted as described above. The samples were probed separately with radiolabeled RNA probes specific for sense (FIG. 16A, lane 1) and antisense (FIG. 16A, lane 2) prosystemin mRNA (see Examples 6–8, above).

In the wounding experiment the distal leaves of plant 1A4 expressed Inhibitor I at 42 µg/ml leaf juice and Inhibitor II at 41 µg/ml leaf juice in response to wounding. The antisense RNA appeared as a band at approximately 1.7 kilobases (FIG. 16A, lane 2) compared to the prosystemin mRNA at 1 Kb (FIG. 16A, lane 1). southern blot analysis showed that plant 1A4 contained a single copy of the antisense construct. This conclusion was confirmed by self-fertilizing plant 1A4 and analyzing 28F1 progeny by Southern blot analysis. Seven (one quarter) of the 28 F1 progeny did not inherit the antisense construct. This experiment also demonstrated that the antisense construct was stably inherited in the F1 generation.

Figure 16B:
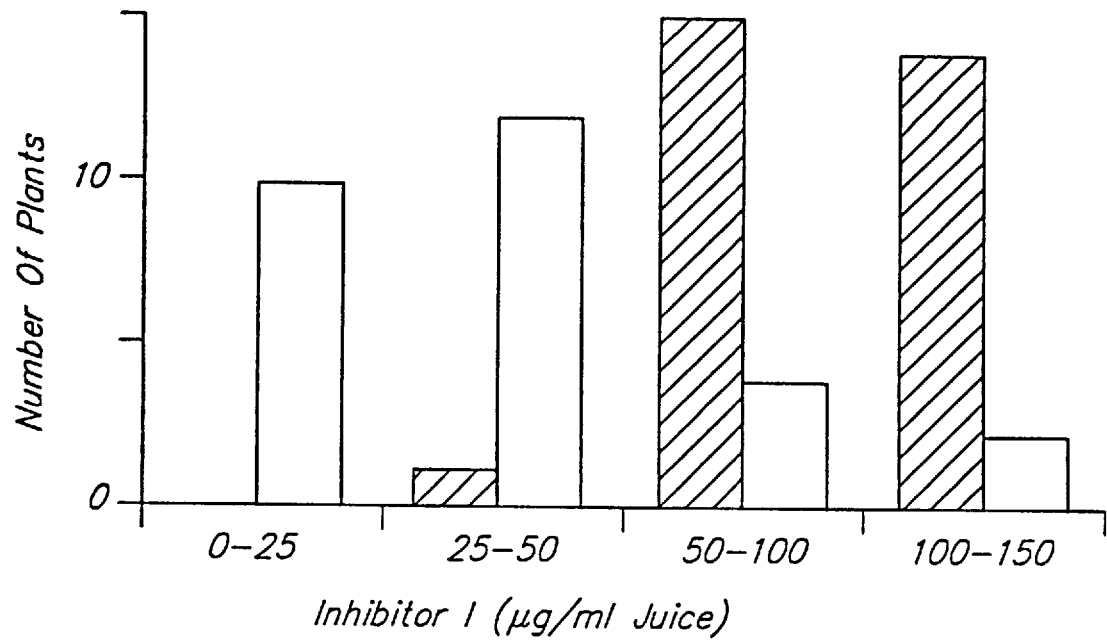
FIG. 16B shows a graphic depiction of the levels of Inhibitor I in wounded F1 transgenic antisense plants (unshaded bars) and non-transformed control plants (solid bars), as described in Example 10, below.
Figure 16C:
FIG. 16C shows a graphical depiction of the levels of Inhibitor II in wounded F1 transgenic antisense plants (unshaded bars) and non-transformed control plants (solid bars), as described in Example 10, below.

To demonstrate that the antisense phenotype segregated with the antisense construct, the levels of Inhibitors I and II in the distal leaves of the 28 F1 plants were measured before wounding, and 24 hr after wounding. FIG. 16B graphically depicts wound-induced accumulation of proteinase Inhibitor I and FIG. 16C depicts wound-induced accumulation of proteinase Inhibitor II in the distal leaves of F1 antisense plants (unshaded bars) and untransformed controls (solid bars). Antisense plant 1A4 was self-fertilized and the amounts of wound-induced proteinase Inhibitors I and II in the distal leaves of three-week old F1 progeny were measured by radial immunodiffusion assay (as described below). The plants had an upper and a lower leaf and a small apical leaf. The lower leaf was wounded and 24 hours later juice was expressed from the upper, unwounded leaf and assayed. The amount of Inhibitor I was measured in 28 F1 plants while the level of Inhibitor II was measured in 27 of the 28 F1 plants. A control group of thirty untransformed tomato plants, var. Better Boy, was also wounded and the amounts of Inhibitors I and II were measured. Inhibitor proteins were not detected in juice expressed from the leaves of six unwounded antisense plants and six unwounded control plants. Three quarters of the antisense plants (i.e., those inheriting the antisense construct), responded weakly to wounding compared to the control population of untransformed plants (FIGS. 16B AND 16C). Plants not inheriting the construct produced levels of proteinase inhibitors equal to those of the untransformed control plants.

In six of the 28 F1 antisense plants Inhibitor I synthesis in the distal leaf was less than 15% of the mean control level of 97.2+/−4.7 µg/ml while Inhibitor II synthesis was undetectable in the distal leaf (mean control level of 122.3+/−7.2 µg/ml). Southern blot analysis of the six least responsive F1 plants suggests that these plants inherited two copies of the antisense construct, although this conclusion must be confirmed by self-fertilizing the plants and demonstrating that none of the F2 progeny produce proteinase inhibitors in response to wounding at levels equal to those of the control plants.

These experiments show that expression of antisense prosystemin mRNA in tomato inhibits the systemic induction of proteinase inhibitor syntheses in response to wounding. It is inferred that antisense prosystemin mRNA prevents the efficient production of prosystemin and, hence, of the mobile systemic wound-signal systemin.

Materials and Methods:

A 747 bp fragment of the prosystemin cDNA was excised from pSYS 1 as a BamHI-Hind III fragment. The BamHI site is located in the bluescript polylinker close to the 5'-end of the cDNA, while the Hind III site is within the cDNA at nucleotide 859 as numbered in FIGS. 7A and 7B. The antisense cDNA fragment thus contained all of the prosystemin mRNA sequence except for the first seven bp of the coding region, all of the 5'-untranslated region and the last 92 bp of the 3'-untranslated region. The cDNA fragment was placed under the control of the constitutive CaMV 35S promoter by cloning it (in the antisense 3' to 5' orientation), into the polylinker of the binary vector pGA643 digested with Bg1 II and Hind III. The antisense construct was transformed into Agrobacterium strain LBA 4404 and the recombinant bacteria were used to transform tomato var. Better Boy.

Tomato seeds, var. Better Boy, were sterilized by soaking for 15 min in a 15% (v/v) solution of Chlorox containing two or three drops of Tween 20. The seeds were washed four times with distilled water then geminated on medium containing: MS salts (4.3 g/L), agarose (6g/L) and thiamine (1 mg/L), pH 5.8. The geminating plants were grown at 28° C. with 16 hr days. Eighty percent of the seeds germinated. After 7–10 days, when the first true leaves appeared, the cotyledons were removed from the seedlings and cut into cubes of edge length 0.2–0.5 cm. The tissue cubes were preconditioned on tobacco feeder plates for two days at 25° C. in the dark. Tobacco feeder plates were prepared by subculturing tobacco (NT-1) suspension cells in medium containing: MS sales (4.3 g/L), sucrose (30 g/L), inositol (0.1 g/L), thiamine (1 mg/L), 2, 4-D (0.2 mg/L) and $KH_2PO_4$ (0.18 g/L) at pH 5.8. The cells were incubated for four days at 25° C. in the dark. The cells were plated over the same medium including 0.7% agarose, then incubated under the same conditions as before for a further two days. Pieces of tomato cotyledon were placed on Whatman No. 4 filter paper soaked in tobacco feeder plate medium and overlaid onto the tobacco feeder plates. The pieces of preconditioned tissue were punctured with a 20-gauge needle and infected with Agrobacterium by soaking them for thirty min in 15 mL of germination medium containing $10^8$ cells/mL. The tissue was blotted dry with sterile filter paper and incubated on tobacco feeder plates for a further two days at 25° C. in the dark. The tissue pieces were then washed three times in germination medium, the third wash containing 0.5 g/L of Cefotaxime. The tissue pieces were blotted dry with sterile filter paper and placed on shooting medium containing: MS sales (4.3 g/L), thiamine (10 mg/L), nicotinic acid (1 mg/L), pyridoxine (1 mg/L), inositol (100 mg/L), sucrose (30 g/L), BAP (2.5 mg/L), IAA (1 mg/L), cefotaxime (250 mg/L), carbenicillin (500 mg/L), kanamycin (100 mg/L) and 0.7% (w/v) agarose. The explants were transferred after the first three days of culture and weekly thereafter. Once callus growth was observed (after the third subculture) the explants were transferred to shooting medium from which the IAA and BAP had been removed and zeatin (2 mg/L) added. Once the shoots were 2–3 inches tall they were transferred to rooting medium which differed from shooting medium in the BAP, cefotaxime and carbenicillin were absent, vancomycin (0.5 g/L) was added and the concentrations of sucrose (20 g/L), kanamycin (20 mg/L) and IAA (0.05 mg/L) were reduced.

EXAMPLE 11

Effect of Growth on *Manduca sexta* Larvae Feeding on Transgenic Plants

Figure 17:
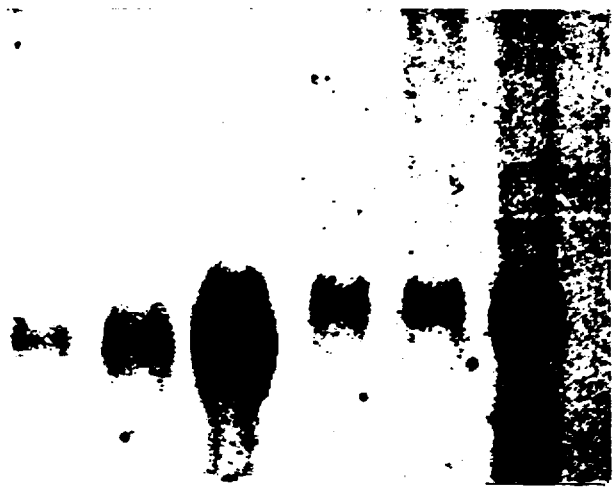
FIG. 17 shows a Northern blot analysis of total RNA extracts collected at different times from undamaged leaves of control (nontransformed) and transgenic tomato plants during the feeding experiments with *Manduca sexta* larvae, as described in Example 11, below.

Northern blot analysis of total RNA extracts, collected at different times from undamaged leaves of control (nontransformed) and transgenic tomato plants was performed during feeding experiments with *Manduca sexta* larvae. Plants were approximately 18 inches in height, having 2–3 main stems. Total RNA from each sample was separated by electrophoresis, blotted onto nitrocellulose paper and probed with a nick-translated $^{32}$P-prosystemin cDNA. The results are shown in FIG. 17.

Figure 18:
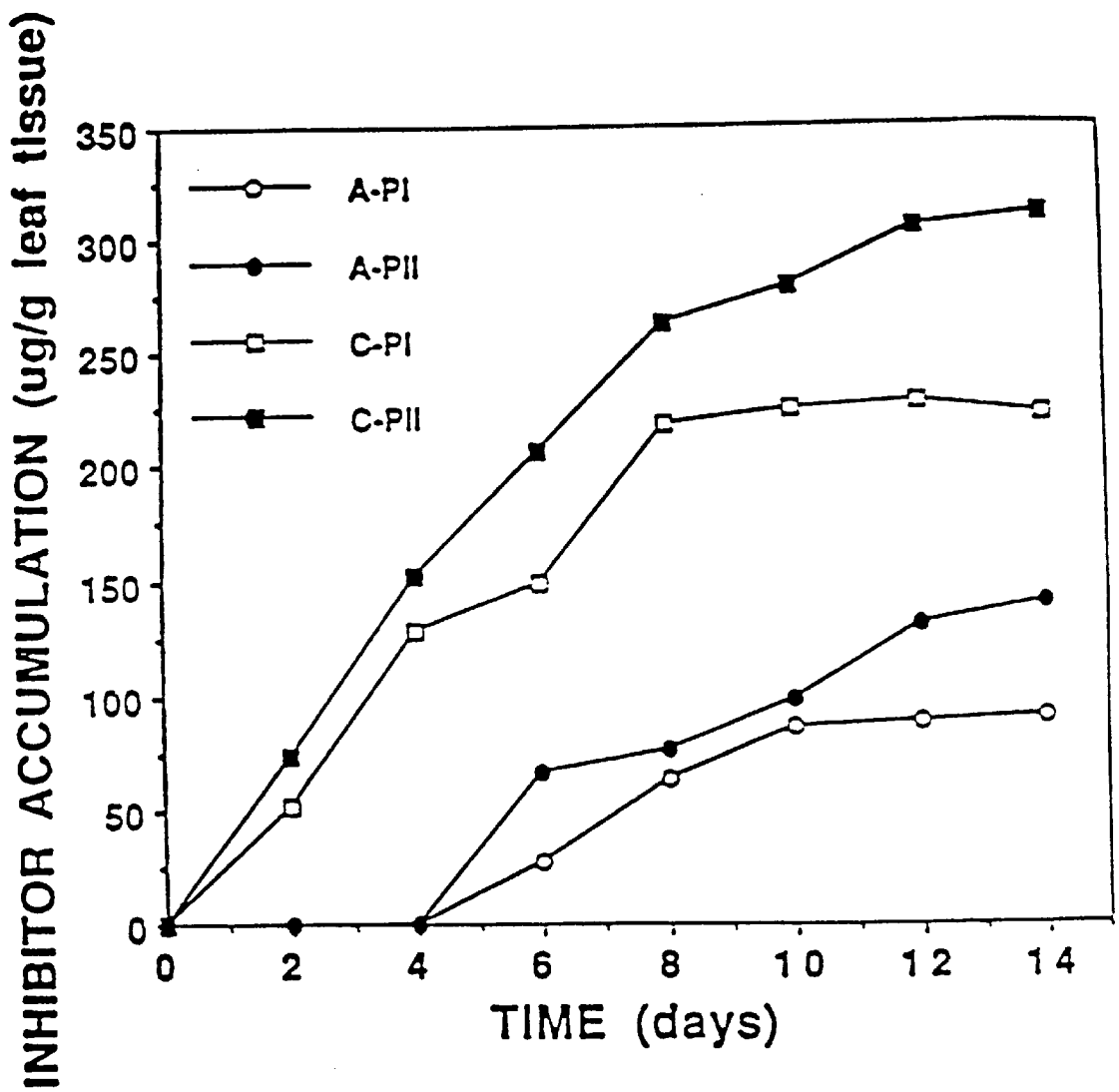
FIG. 18 shows the time course of accumulation of Inhibitor I and 11 proteins in undamaged leaves of control and transgenic tomato plants induced by the feeding of *Manduca sexta* larvae, as described in Example 11, below.

The accumulation of Inhibitor I and II proteins in undamaged leaves of control and trasgenic antisense tomato plants, induced by feeding on *Manduca sexta* larvae was measured. Leaf juice was expressed with a mortar and pestle and assayed by radial immunodiffusion assay (Ryan, 1967). As shown in FIG. 18, transgenic antisense tomato plants showed decreased accumulation of both Inhibitor I and II proteins. In FIG. 18, A=transgenic antisense plants, C=wild type plants, PI=Inhibitor I and PII=Inhibitor II.

Figure 19:
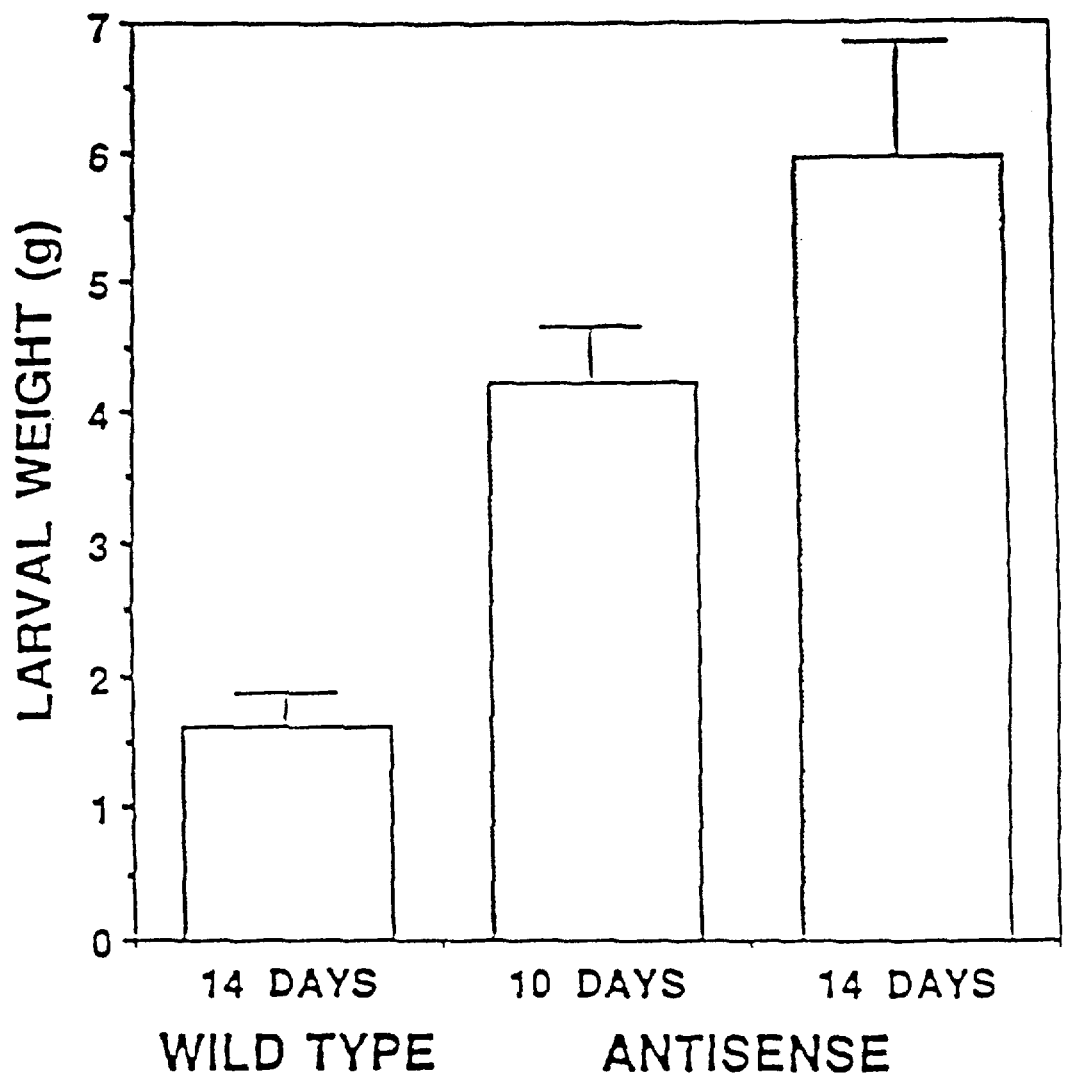
FIG. 19 shows the growth of *Manduca sexta* larvae, while feeding on leaves of control and transgenic antisense tomato plants, as described in Example 11, below.

The growth of *Manduca sexta* larvae, while feeding on leaves of control and transgenic antisense tomato plants was measured. Ten first instar larvae were placed randomly on each of six control (wild tape) and transgenic plants and removed and weighed. Those larvae feeding on control plants were weighed at 14 days and those feeding on transgenic antisense plants were weighed at 10 and 14 days. As shown in FIG. 19, those larvae feeding on transegenic antisense plants showed increased growth weight over those feeding on wild type plants. Values in FIG. 19 are the average from three different plant experiments, statistical significance is shown.

Figure 20:
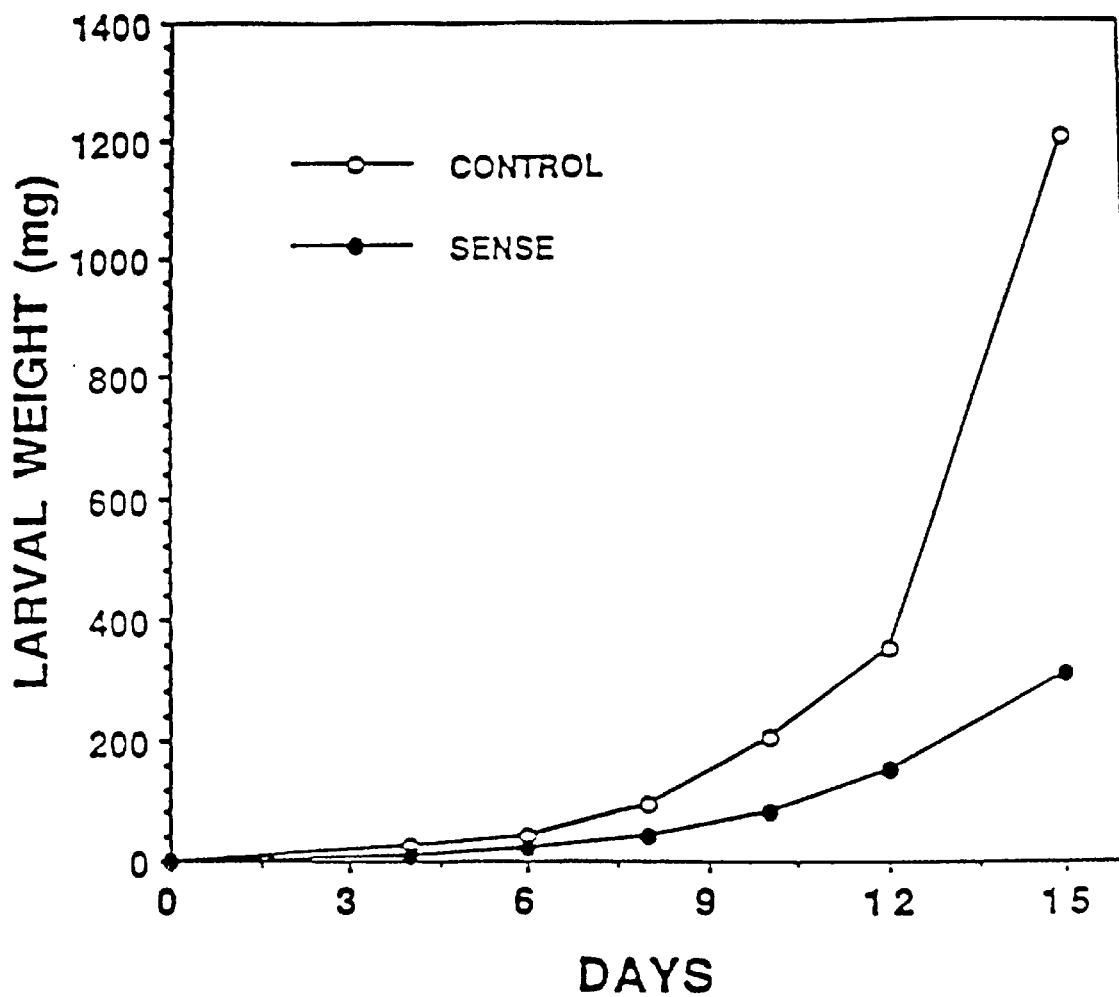
FIG. 20 shows the time course of larval weight gain of *Manduca sexta* larvae feeding on leaves of wild type and transgenic tomato plants, as described in Example 11, below.

Transgenic plants containing a prosystemin gene driven by a CaMV promoter (Example 10, above) were produced. The prosystemin gene was essentially the same as the antisense gene (McGurl et al., *Science* 255, 1570–1573), except the prosystemin cDNA was in the sense orientation. *Manduca sexta* larvae were allowed to feed on leaves of control (wild type) and transgenic sense tomato plants. The control leaves contained little or no Inhibitor I or II. The leaves of the transgenic plant expressing prosystemin contained about 300 µ/g tissue Inhibitor I and about 200 µ/g tissue Inhibitor II. As shown in FIG. 20, the weight of larvae feeding on the control leaves increased at a faster rate than the larvae feeding on the transgenic sense leaves. Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the specification and following claims.

All publications and applications cited herein are incorporated by reference.

CITATIONS

1. C. A. Ryan, *Ann. Rev. Phytopathol.* 28, 425 (1990).
2. D. J. Bowles, *Ann. Rev. Biochem.* 59, 873 (1990).
3. M. Chessin and A. E. Zipf, *The Botanical Review* 56, 193 (1990).
4. D. L. Dreyer and B. C. Campbell, *Plant, Cell and Environ.* 10, 353 (1987).
5. T. R. Green and C. A. Ryan, *Science* 175, 776 (1972).
6. C. A. Ryan, *TIBS* 3, No. 7, 148 (1978).
7. V. A. Hilder, A. M. R. Gatehouse, S. E. Sheerman, R. F. Barker, D. Boulter, *Nature* 330, 160 (1987).
8. R. Johnson, J. Narvaez, G. An, C. A. Ryan, *Proc. Natl. Acad. Sci. U.S.A.* 86, 9871 (1989).
9. J. S. Graham, G. Hall, G. Pearce, C. A. Ryan, *Planta* 169, 399 (1986).
10. J. S. Graham, G. Pearce, J. Merryweather, K. Titani, L. Ericsson, C. A. Ryan, *J. Biol. Chem.* 260, No. 11, 6555 (1985).
11. J. S. Graham, G. Pearce, J. Merryweather, K. Titani, L. H. Ericsson, C. A. Ryan, *J. Biol. Chem.* 260, No. 11, 6561 (1985).
12. C. A. Ryan, Plant Physiol. 43, 1880 (1968).
13. W. E. Brown and C. A. Ryan, *Biochemistry* 23, 3418 (1984).
14. W. E. Brown, K. Takio, K. Titani, C. A. Ryan, *Biochemistry* 24, 2105 (1985).
15. D. Roby, A. Toppan, M. T. Esquerre-Tugaye, *Physiol. Mol. Pl. Pathol.* 30, 6453 (1987).
16. H. D. Bradshaw, J. B. Hoflick, T. J. Parsons, H. R. G. Clarke, *Plant Mol. Biol.* 14,51 (1989).
17. C. A. Ryan and E. E. Fanner, *Annu. Rev. Plant. Physiol. Mol.Bio.* 42, 651 (1991).
18. E. E. Farmer and C. A. Ryan, *Proc. Natl. Acad. Sci. U.S.A.* 87, 7713 (1990).
19. H. Pena-Cortes, J. J. Sanchez-Serrano, R. Mertens, L. Willmitzer, S. Prat, *Proc. Natl. Acad. Sci. U.S.A.* 86, 9851 (1989).
20. E. Davies, *Plant, Cell and Environ.* 10, 623 (1987).
21. J. F. Thain, H. M. Doherty, D. J. Bowles, D. C. Wildon, *Plant, Cell and Environ.* 13, 569 (1990).
22. G. Pearce, D. Strydom, S. Johnson, C. A. Ryan, *Science* 253, 895 (1991).
23. B. McGurl, G. Pearce and C. A. Ryan, *Plant Molecular Biology*, submitted.
24. H. A. Lutcke et al., *EMBO Journal* 6, 43 (1987).
25. R. B. Harris, *Arch. Biochem. Biophys.* 275, No. 2, 315 (1989).
26. J. Douglass, O. Civelli and E. Herbert, *Ann. Rev. Biochem.* 53, 665 (1984).
27. L. J. Jung and R. H. Schefler, *Science* 251, 1330 (1991).
28. C. A. Ryan, *Anal. Biochem.* 19, 434 (1967).
29. R. Trautman, K. M. Cowan, G. G. Wagner, *Immunochemistry* 8, 901 (1971).
30. T. P. Hopp and K. R. Woods, *Proc. Nat. Acad. Sci.* 78, 3824 (1981).
31. I. Schechter and A. Berger, *Biochem. Biophys. Res. Commun.* 27,157 (1967).
32. S. O. Rogers and A. J. Bendich, *Plant Mol. Biol.* 5, 69 (1985).

What is claimed is:

1. A polypeptide encoded by a nucleic acid comprising a nucleotide sequence substantially as shown in SEQ. ID. NO. 2.

2. A polypeptide having an amino acid sequence substantially as shown in SEQ. ID. NO. 1.

3. A polypeptide having an amino acid sequence substantially as shown in SEQ: ID. NO. 3.

4. A polypeptide comprising the amino acid sequence $R_1R_1QR_1R_2PPR_1R_2R_2R_1PPR_2R_1QR_1R_1$, wherein $R_1$ is any amino acid, $R_2$ is lysine or arginine, Q is glutamine, and P is proline.

5. The polypeptide of claim 4, wherein the polypeptide comprises the amino acid sequence $NH_3$-AVQSKPPSKRDPPKMQTD-COO-.

6. An amino acid sequence translated from substantially pure systemin mRNA.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

-continued ( i ) SEQUENCE CHARACTERISTICS:
    ( A ) LENGTH: 200 amino acids
    ( B ) TYPE: amino acid
    ( D ) TOPOLOGY: linear ( i i ) MOLECULE TYPE: polypeptide
    ( A ) DESCRIPTION: prosystemin #1- #200;systemin #179-196;
    Figure 6- 7.

( i x ) SEQUENCE DESCRIPTION: SEQ ID NO:1:

```
Met Gly Thr Pro Ser Tyr Asp Ile Lys Asn Lys Gly Asp Asp Met Gln
 1           5                  10                  15

Glu Glu Pro Lys Val Lys Leu His His Glu Lys Gly Gly Asp Glu Lys
            20                  25                  30

Glu Lys Ile Ile Glu Lys Glu Thr Pro Ser Gln Asp Ile Asn Asn Lys
        35                  40                  45

Asp Thr Ile Ser Ser Tyr Val Leu Arg Asp Asp Thr Gln Glu Ile Pro
        50                  55                  60

Lys Met Glu His Glu Gly Gly Tyr Val Lys Glu Lys Ile Val Glu
65                  70                  75                  80

Lys Glu Thr Ile Ser Gln Tyr Ile Ile Lys Ile Glu Gly Asp Asp Asp
                85                  90                  95

Ala Gln Glu Lys Leu Lys Val Glu Tyr Glu Glu Glu Glu Tyr Glu Lys
                100                 105                 110

Glu Lys Ile Val Glu Lys Glu Thr Pro Ser Gln Asp Ile Asn Asn Lys
            115                 120                 125

Gly Asp Asp Ala Gln Glu Lys Pro Lys Val Glu His Glu Glu Gly Asp
            130                 135                 140

Asp Lys Glu Thr Pro Ser Gln Asp Ile Ile Lys Met Glu Gly Glu Gly
145                 150                 155                 160

Ala Leu Glu Ile Thr Lys Val Val Cys Glu Lys Ile Ile Val Arg Glu
                165                 170                 175

Asp Leu Ala Val Gln Ser Lys Pro Pro Ser Lys Arg Asp Pro Pro Lys
            180                 185                 190

Met Gln Thr Asp Asn Asn Lys Leu
        195                 200
```

( 2 ) INFORMATION FOR SEQ ID NO:2:

( i ) SEQUENCE CHARACTERISTICS:
        ( A ) LENGTH: 951 bases
        ( B ) TYPE: nucleic acid
        ( C ) STRANDEDNESS: single
        ( D ) TOPOLOGY: linear ( i i ) MOLECULE TYPE: cDNA
        ( A ) DESCRIPTION: prosystemin cDNA; start ATG at #105

( i x ) SEQUENCE DESCRIPTION: SEQ ID NO:2:

```
AAAATTAAAT TTGATATTTG GTTAACTCG  ATTTTCCATG AACACCCTTA GTGATGAGTA   60
TATAAAGCTC AGCTCATGAA GAGTTGAAAT AAACTAAGAA AACCATGGGA ACTCCTTCAT  120
ATGATATCAA AAACAAGGA  GATGACATGC AAGAAGAACC AAAGGTGAAA CTTCACCATG  180
AGAAGGGAGG AGATGAAAAG GAAAAATAA  TTGAAAAAGA GACTCCATCC CAAGATATCA  240
ACAACAAAGA TACCATCTCT TCATATGTTT TAAGAGATGA TACACAAGAA ATACCAAAGA  300
TGGAACATGA GGAGGGAGGA TATGTAAAGG AGAAAATTGT TGAAAAGGAG ACTATATCCC  360
AATATATCAT CAAGATTGAA GGAGATGATG ATGCACAAGA AAAACTAAAG GTTGAGTATG  420
AGGAGGAAGA ATATGAAAAA GAGAAAATAG TTGAAAAAGA GACTCCATCC CAAGATATCA  480
```

-continued

| ACAACAAAGG | AGATGATGCA | CAAGAAAAAC | CAAAGGTGGA | ACATGAGGAA | GGAGATGACA | 540 |
| AAGAGACTCC | ATCACAAGAT | ATCATCAAGA | TGGAAGGGGA | GGGTGCACTA | GAAATAACAA | 600 |
| AGGTGGTATG | TGAGAAAATT | ATAGTACGAG | AAGATCTTGC | TGTTCAATCA | AAACCTCCAT | 660 |
| CAAAGCGTGA | TCCTCCCAAA | ATGCAAACAG | ACAATAATAA | ACTCTAGAAA | CATCCAAAAA | 720 |
| AAATTAATAA | ATAAAAAATT | ATAATTCAGA | ACGATAAAGT | AAAAATTCTG | AATTTGTCTC | 780 |
| CCGTTAGAAA | AGTAACTTCA | AATAAATATT | TGTCTTTCTT | TGTATTTTCA | AAGTGTAATT | 840 |
| TGGTTATTGT | ACTTTGAGAA | GCTTTCTTTA | GATTGTTATG | TACTTGTATT | GCTTCCTTTC | 900 |
| TTTTGGCTTA | TTTATATAAT | ATAAATAAAA | AATAAATAAA | TATCTAAAGA | T | 951 |

( 2 ) INFORMATION FOR SEQ ID NO:3:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide
        ( A ) DESCRIPTION: systemin; Figure 3.

( i x ) SEQUENCE DESCRIPTION: SEQ ID NO:3:

```
Ala  Val  Gln  Ser  Lys  Pro  Pro  Ser  Lys  Arg  Asp  Pro  Pro  Lys  Met  Gln  Thr  Asp
 1               5                        10                       15
```

( 2 ) INFORMATION FOR SEQ ID NO:4:

( i ) SEQUENCE CHARACTERISTICS:
        ( A ) LENGTH: 4526 bases
        ( B ) TYPE: nucleic acid
        ( C ) STRANDEDNESS: single
        ( D ) TOPOLOGY: linear ( i i ) MOLECULE TYPE: DNA
        ( A ) DESCRIPTION: prosystemin genomic DNA; Figures 8A-8C.

( i x ) SEQUENCE DESCRIPTION: SEQ ID NO:4:

| AAAATTAAAT | TTGATATTTG | GTTTAACTCG | ATTTTCCATG | AACACCCTTA | GTGATGAGTA | 60 |
| TATAAAGCTC | AGCTCATGAA | GAGTTGAAAT | AAACTAAGAA | AACCATGGGA | ACTCCTTCAT | 120 |
| ATGATATCAA | AAACAAAGGT | ATCATTTCTT | TATATGCCTA | AGTATATATT | TATTTATATA | 180 |
| TTTTGTAACT | AAAATTTTAT | ATTAAAATCA | ACAAGTGAGA | GTTTAACAAA | AATCATATTA | 240 |
| AAGAAAAAAA | ATATATTAAT | TTTTAATCAT | GGTATTATCC | TCCAGGAGAT | GACATGCAAG | 300 |
| AAGAACCAAA | GGTGAAACTT | CACCATGAGA | AGGTAACTTT | AGTTCTCCT | TTTTCTTTTT | 360 |
| TCAACTTCTT | TATATATTAT | TTTTGTAAAT | TTTTTTATAT | TATAATGTTC | AAATGGTCTC | 420 |
| ATTTTCTAAT | TAATAATGTG | TCTGAATCGC | CATGTTATTT | ATGTTAGATT | TAATACATTA | 480 |
| ATAACATTGT | TAGTAAATGT | TAGAATACTG | ACTCCCAAAT | TCGCTTAAGG | AACAAGTATA | 540 |
| TTTCATGTGT | TTCTTTGCAG | ATAACAATAA | TTATGTTTTG | TAAAGCAAAT | AAAATAATAA | 600 |
| CATAATATTT | TATCGTAGAA | AACTCCAACT | CATTATTTAG | ATATTTAGAT | TATGATTTGC | 660 |
| TTTAATTATA | CTTTTTTAAA | CATGATAAAT | TATTTCTGTT | AGACATTTTC | GATTCATTTT | 720 |
| TTTTTTTACA | AAAATTGTAT | TTGCTCTCAA | ACGTTACTA | GTTAGTTAAG | TTAACTATAC | 780 |
| AAAATATGTC | ATCTCATTTG | ATTATATACA | TCAGGCTCAA | TTAAAACATA | TTGGAGATAT | 840 |
| GGAGATTTTA | CGATTCATTA | ACACTAATGT | GTATAGTTAG | AAAATGTGAA | ATATTTCAAA | 900 |
| TGGTTAACTT | TTCTGTATAA | TTGACATTTG | AAACTATATG | TTTAATTATA | ACAAACCGTA | 960 |
| ATCAAATGTT | CAAATAAAAT | TGAATGACAA | TAGGTATAAG | GAGCTATCAA | TATATTAGCT | 1020 |

| | | | | | | |
|---|---|---|---|---|---|---|
| CTTCTTGATT | CAACTTATTT | ACCGTTATAA | TTAAATAATG | ACTCGTTAAT | TGATTTAATT | 1080 |
| TTTTTACTCA | CGTGAAATGA | TTTAATCAAC | TCATTTATCA | CCCTTATTTA | CGACTCATGT | 1140 |
| AGAATAATGT | TCTTTATACT | TGTATACAAT | TTACTCGGAT | ATTTTTTTA | AATTTTTTT | 1200 |
| TATGTTTAAT | TAAATACTAT | TAAAATGAAG | AAATATTATT | TATAATTGAA | GAATATTGAA | 1260 |
| TTTTTTTTCC | ATCAAAATTT | ACAGGGAGGA | GATGAAAAGG | AAAAAATAAT | TGAAAAGAG | 1320 |
| ACTCCATCCC | AAGATATCAA | CAACAAAGAT | ACCATCTCTT | CATATGTTTT | AAGTATTTAA | 1380 |
| TTTTTTTCAA | TCTTTTTTTT | TTCTCATCTT | CTTATTTTAA | TCATCTAAAA | GAAATTATTA | 1440 |
| TTATGTTTTT | TTTTAACTTT | AATTATAATA | TTATCCAGCA | GGAGATGATA | CACAAGAAAT | 1500 |
| ACCAAAGATG | GAACATGAGG | AGGTAACTAT | ATATTTCAAT | TTATTTACTA | ATTTATAAAT | 1560 |
| AATGACTTAT | TCATTGATTC | AATTTATTTT | AATTCGTTTG | AAATCAAACT | AAGGTTACCA | 1620 |
| TATTATCACC | CCACTCCCTC | CACTACTCAT | TTAAATGAT | GGTTTGATAC | TTTGCATGCA | 1680 |
| ATTTGTTTA | TTCATAAGTC | ATTTATTTTT | CAAAATTTT | ATGTTCAGTT | AAACGTTTGC | 1740 |
| ATACATTTG | TTTATACATA | ATTCATCTAT | TTCTTTAAA | ATTTATGTT | CAGTTAAACG | 1800 |
| ATTGCATACA | TTTTGTTCAT | ACATAAGTCA | TCTATTTTT | TAAAAAAAA | TTATGTTCAG | 1860 |
| TTAACGTTTG | CATACAATTT | TGTTCATACA | TAATTCATCT | ATTTTTTAA | AATTTATGA | 1920 |
| TCAGTTAAAC | TTTTATATAC | AATTTTGCTC | GTACATAAGT | CATCTATTTT | TTTAAAATTT | 1980 |
| TATGTTCAGT | TAAACGTAAT | AAATAAAATT | AGACTGTGGA | AATATTATTT | ATTATTAAAG | 2040 |
| GATATTACAG | GGAGGATATG | TAAAGGAGAA | AATTGTTGAA | AAGGAGACTA | TATCCCAATA | 2100 |
| TATCATCAAG | ATTGAAGGTA | TAATCTATTT | ATATGTGTCT | AAATATTTAA | TTTTATTTTT | 2160 |
| ATTTTTCAGA | TTTTTTAGTA | AGGGATTTTT | TTATTTTTTT | TCAAAAATG | TGAATCATTT | 2220 |
| TCAAGAAGTT | AATATTATTT | TTGGTAACTT | TAATCTTGAT | ATATTATTCT | CCAGGAGATG | 2280 |
| ATGATGCACA | AGAAAAACTA | AAGGTTGAGT | ATGAGGAGGT | AACTTTAATT | TCTTCTTTGA | 2340 |
| CTTTTTATTT | ATTATTTTTG | TATATTTTAC | TGTCTATTTA | TTTCATATTC | ACAAATTATA | 2400 |
| TTTATCACAT | ATATATTGCT | TTATTTTCTT | CAAAATTACA | GGAAGAATAT | GAAAAGAGA | 2460 |
| AAATAGTTGA | AAAAGAGACT | CCATCCCAAG | ATATCAACAA | CAAAGGTATA | TATCATATCT | 2520 |
| TCATATGCCT | AAGATTTTAT | TTCTTCTTA | TTTTTCATAT | TATTTTTATT | TAACTAAATT | 2580 |
| TAGTATGAAA | CCTTTTTTTT | TTTAAAAAAA | TCATCTTAAA | TAAAATATTA | TTTTTGGGTG | 2640 |
| ACTCAAATCA | TTGACCTTAT | ATATTCTCCA | GGAGATGATG | CACAAGAAAA | ACCAAAGGTG | 2700 |
| GAACATGAGG | TAACTACTTA | TATTTTTCTC | TCTCTTTATT | ACATAAAATC | ACATTAGTTA | 2760 |
| TATGATAATT | GGCTATGCTA | ATAATAAAAA | AACAATTAAT | ATATTTATAG | GAATTTAAAC | 2820 |
| AGGGTGGAGT | GTCCATGATC | TTTATTTTTA | TCTTGTAAAG | TTACTAAGAC | TATTTCCAAA | 2880 |
| TAGACCTTTA | GTTTGAGCAA | AATCTATCAG | AAAATACGAT | AATAAGAAG | TCACGCTGAA | 2940 |
| AATAAAATAT | TAATTTTGTG | ACGTGAAAGC | AATATCAAGA | GCCCCGTCAA | TTTGTTGTAT | 3000 |
| TATGTCAGAT | GCAACATCCT | TCTTTCTTCT | CGTGAAGTAT | AGGAGCGCTT | AGCACACATC | 3060 |
| TCAACATAAT | GCGCGATAAT | AACGTTTAA | TGGTGAATCT | ATCGGTATCA | TAACAATAGT | 3120 |
| ATACAACTTT | AAACCTAATG | ATCGTCTAGC | TAGTAATCTT | TCAAAATGAG | GGACCCTAAT | 3180 |
| TACTGACAAA | ATTTGTGTCT | AACATAACTT | ATGTACCATA | ACAATAATAT | ATCTTGTGTA | 3240 |
| ATTTATGAGT | GAAGGTAGGG | TTTGAAATTA | AACATAATCA | ATAAAATTGG | ACAAAGAGA | 3300 |
| TATTATTTAT | TAATTGAAAG | ATATTAATAG | TTTTTTTCTT | CAAAATTACA | GGAAGGAGAT | 3360 |
| GACAAAGAGA | CTCCATCACA | AGATATCATC | AAGATGGAAG | GTATCAATCT | ATTTATATTT | 3420 |

| | | | | | |
|---|---|---|---|---|---|
| TTTATAAGTA | TTTTTTTCTT | ACAATTTTTT | TATTTCCTTT | GGTATATATG | AAACTATTTT | 3480
| TTTTAACCAT | CTTTAAAAAA | AAATAATACT | TATGTATAAC | TATAATCATG | ATATTATCAT | 3540
| CCAGGGGAGG | GTGCACTAGA | AATAACAAAG | GTGGTATGTG | AGGTAACTAA | ATTTCTTCTT | 3600
| CCAATTTTTC | TATACATTAT | GTTTGTATTT | TTTTTTTTGG | ATTCATTCGA | ACTTTCTTCG | 3660
| ATAGAAAGTC | TTGCTATCTA | TATACGATTA | AAATTATATT | GAGTTTACGA | TAAAAATATA | 3720
| TTTAAACAAT | TCTTTTTTTA | ATTTCATATC | TAAACTATTG | AAAATGTGTC | TGCCCTCGTA | 3780
| ACCTCGGTAC | AAAGCCAACT | AGAACCACAT | TTTAAATGAT | TAAAAAAATC | TTTTGAAAGT | 3840
| GTGAGAAATA | CGCTGAAACT | ATCGCTTATT | ATTTTATTTT | TACGTATATG | CAATAGACAA | 3900
| TATTGAATCC | TCTTCTATTT | ATTCGTATGT | TTACTTCCTC | ACATATCAAA | TCTCTTAGTA | 3960
| AAAATTCTGA | CTTCACCACT | GTATATATCT | TTTTATTTTG | ATTTTGATT | GCATTTCATT | 4020
| TGTTTAGTTA | TAATAACTAA | TAAGGGTCTT | TTATTTTATT | TATAGCATGA | TGCTACTATT | 4080
| TTTTGGACAC | TACAAGGAGC | ATACAATTCA | AATCTCAAAC | TTTTTTATAT | TTTTTTTCTA | 4140
| TATTTTTTAT | TATAAAAGGA | TATTAATTTC | TTTTTTCTTT | CAAATACAGA | AAATTATAGT | 4200
| ACGAGAAGAT | CTTGCTGTTC | AATCAAAACC | TCCATCAAAG | CGTGATCCTC | CCAAAATGCA | 4260
| AACAGACAAT | AATAAACTCT | AGAAACATCC | AAAAAAAATT | AATAAATAAA | AAATTATAAT | 4320
| TCAGAACGAT | AAAGTAAAAA | TTCTGAATTT | GTCTCCCGTT | AGAAAGTAA | CTTCAAATAA | 4380
| ATATTTGTCT | TTCTTTGTAT | TTTCAAAGTG | TAATTTGGTT | ATTGTACTTT | GAGAAGCTTT | 4440
| CTTTAGATTG | TTATGTACTT | GTATTGCTTC | CTTCTTTTG | GCTTATTTAT | ATAATATAAA | 4500
| TAAAAAATAA | ATAAATATCT | AAAGAT | | | | 4526

( 2 ) INFORMATION FOR SEQ ID NO:5:

( i ) SEQUENCE CHARACTERISTICS:
        ( A ) LENGTH: 59 bases
        ( B ) TYPE: nucleic acid
        ( C ) STRANDEDNESS: single
        ( D ) TOPOLOGY: linear ( i i ) MOLECULE TYPE: DNA
        ( A ) DESCRIPTION: Figure 11A, con.

( i x ) SEQUENCE DESCRIPTION: SEQ ID NO:5:

| | | | | | |
|---|---|---|---|---|---|
| GAGAATGAAA | GAAAAATAGT | TGAAAAGAG | ACTCCATCCC | AAGATATCAA | CAACAAAGA | 59

( 2 ) INFORMATION FOR SEQ ID NO:6:

( i ) SEQUENCE CHARACTERISTICS:
        ( A ) LENGTH: 39 bases
        ( B ) TYPE: nucleic acid
        ( C ) STRANDEDNESS: single
        ( D ) TOPOLOGY: linear ( i i ) MOLECULE TYPE: DNA
        ( A ) DESCRIPTION: Figure 11B, con.

( i x ) SEQUENCE DESCRIPTION: SEQ ID NO:6:

| | | | |
|---|---|---|---|
| GAGATGATGC | ACAAGAAAAA | CCAAAGGTGG | AACATGAGA | 39

( 2 ) INFORMATION FOR SEQ ID NO:7:

( i ) SEQUENCE CHARACTERISTICS:
        ( A ) LENGTH: 28 bases
        ( B ) TYPE: nucleic acid
        ( C ) STRANDEDNESS: single
        ( D ) TOPOLOGY: linear ( i i ) MOLECULE TYPE: DNA (A) DESCRIPTION: Figure 14, Exon 3.

(ix) SEQUENCE DESCRIPTION: SEQ ID NO:7:

AAGATACCAT CTCTTCATAT GTTTTAAG                28

(2) INFORMATION FOR SEQ ID NO:8:

(i) SEQUENCE CHARACTERISTICS:
      (A) LENGTH: 27 bases
      (B) TYPE: nucleic acid
      (C) STRANDEDNESS: single
      (D) TOPOLOGY: linear (ii) MOLECULE TYPE: DNA
      (A) DESCRIPTION: Figure 14, Exon 7.

(ix) SEQUENCE DESCRIPTION: SEQ ID NO:8:

AAGATATCAT ATCTTCATAT GCCTAAG                 27